US008586632B2

(12) United States Patent
Peyrot Des Gachons et al.

(10) Patent No.: US 8,586,632 B2
(45) Date of Patent: Nov. 19, 2013

(54) USE OF THE IRRITATING PRINCIPAL OLEOCANTHAL IN OLIVE OIL, AS WELL AS STRUCTURALLY AND FUNCTIONALLY SIMILAR COMPOUNDS

(75) Inventors: Catherine Peyrot Des Gachons, Philadelphia, PA (US); Jeffrey B. Sperry, Philadelphia, PA (US); Bruce Bryant, Elkins Park, PA (US); Paul A. S. Breslin, Highland Park, NJ (US); Amos B. Smith, III, Merion, PA (US); Gary K. Beauchamp, Philadelphia, PA (US)

(73) Assignees: Monell Chemical Senses Center, Philadelphia, PA (US); The Trustees of The University of Pennsylvania, Philadelphia, PA (US)

( * ) Notice: Subject to any disclaimer, the term of this patent is extended or adjusted under 35 U.S.C. 154(b) by 691 days.

(21) Appl. No.: 12/597,053

(22) PCT Filed: Apr. 25, 2007

(86) PCT No.: PCT/US2007/067393
§ 371 (c)(1),
(2), (4) Date: Sep. 21, 2010

(87) PCT Pub. No.: WO2007/133908
PCT Pub. Date: Nov. 22, 2007

(65) Prior Publication Data
US 2011/0020424 A1    Jan. 27, 2011

(51) Int. Cl.
*A61K 31/22* (2006.01)
*A61K 31/215* (2006.01)

(52) U.S. Cl.
USPC ........... 514/546; 514/530; 514/506; 514/529; 514/532; 514/549; 560/174; 560/177

(58) Field of Classification Search
None
See application file for complete search history.

(56) References Cited

U.S. PATENT DOCUMENTS 2,967,128 A    1/1961 Kare
4,790,990 A    12/1988 Mason et al.

FOREIGN PATENT DOCUMENTS

WO    WO 2007/133908    11/2007

OTHER PUBLICATIONS

Morita et al., An organozine aid in alkylation and acylation of lithium enolates, 1989, J. Org. Chem., vol. 54, No. 8, pp. 1785-1787.*
Andrewes et al., "Sensory Properties of Virgin Olive Oil Polyphenols: Identification of Deacetoxy-Ligstroside Aglycon as a Key Contributor to Pungency", J. Agric. Food Chem., Feb. 26, 2003, 51(5), 1415-1420.
Anke et al., "Comparison of the Antimicrobial and Cytotoxic Activities of Twenty Unsaturated Sesquiterpene Dialdehydes From Plants and Mushrooms", Planta Med., Aug. 1991, 57(4), 344-346.
Appendino et al., "Chemoselective Esterification of Phenolic Acids and Alcohols", Org. Lett., Oct. 31, 2002, 4(22), 3839-3841.
Baldioli et al., "Antioxidant Activity of Tocopherols and Phenolic Compounds of Virgin Oil Oil", J. Am. Oil Chem. Soc., Nov. 1996, 73(11), 1589-1593.

(Continued)

*Primary Examiner* — Yate K Cutliff
(74) *Attorney, Agent, or Firm* — Woodcock Washburn LLP

(57) ABSTRACT

The invention provides oleocanthal analogs and methods of using oleocanthals in various formulations including, food additives; pharmaceuticals; cosmetics; animal repellants; and discovery tools for mammalian irritation receptor genes, gene products, alleles, splice variants, alternate transcripts and the like.

10 Claims, 9 Drawing Sheets

(56) References Cited

OTHER PUBLICATIONS

Beauchamp et al., "Ibuprofen-Like Activity in Extra-Virgin Olive Oil", Nature, Sep. 1, 2005, 437(7055), 45-46.
Edmunds et al., "The Wittig Reaction", in Modern Carbonyl Olefination, Takeda, Ed., John Wiley & Sons, NJ, (no month available) 2004, Chapter 1, pp. 1-16.
Jin et al., "Practical Synthesis of D- and 1-2-Cyclopentenone and Their Utility for the Synthesis of Carbocyclic Antiviral Nucleosides Against Orthopox Viruses (Smallpox, Monkeypox and Cowpox Virus)", J. Org. Chem., Nov. 14, 2003, 68(23), 9012-9018.
Johnson et al., "Triply Convergent Synthesis of (−)-prostaglandin E2 Methyl Ester", J. Am. Chem. Soc., Jul. 1988, 110(14), 4726-4735.
Johnson, "Biotransformations in the Synthesis of Enantiopure Bioactive Molecules", Acc. Chem. Res., May 13, 1998, 31(6), 333-341.
Liles et al., "Activation of Protein Kinase C Induces Rapid Internalization and Subsequent Degradation of Muscarinic Acetylcholine Receptors in Neuroblastoma Cells", J. Biol. Chem., Apr. 25, 1986, 261(12), 5307-5313.
Manna et al., "Protective Effect of the Phenolic Fraction From Virgin Olive Oils Against Oxidative Stress in Human Cells", J. Agric. Food Chem., Oct. 23, 2002, 50(22), 6521-6526.
Mitsunobu, "The Use of Diethyl Azodicarboxylate and Triphenylphosphine in Synthesis and Transformation of Natural Products", Synthesis, (no month available) 1981, 1, 1-28.
Montedoro et al., "Simple and Hydrolyzable Compounds in Virgin Olive Oil, 3 Spectroscopic Characterizations of the Secoiridoid Derivatives", J. Agric. Food Chem., Nov. 1993, 41(11), 2228-2234.
Moon et al., "Improved and Alternative Synthesis of D - and L -Cyclopentenone Derivatives, The Versatile Intermediates for the Synthesis of Carbocyclic Nucleosides", Tetrahedron: Asym., Jun. 2002, 13(11), 1189-1193.
Morihara et al., "Selective Inhibition of Abeta42 Production by NSAID R-enantiomers", J. Neurochem., Nov. 2002, 83(4), 1009-1012.
Morita et al., "An Organozinc Aid in Alkylation and Acylation of Lithium Enolates" J. Org. Chem., Apr. 1989, 54(8), 1785-1787.

Nishiyama et al., "New Stereocontrolled Approach to Some Insect Pheromones via Silicon-Directed Beckmann Fragmentation", Tetrahedron Lett., (no month available) 1984, 25(2), 223-226.
Owen et al., "Phenolic Compounds and Squalene in Olive Oils: The Concentration and Antioxidant Potential of Total Phenols, Simple Phenols, Secoiridoids, Lignansand Squalene", Food & Chemical Toxicology, Aug. 2000, 38(8), 647-659.
Owen et al., "The Antioxidant/Anticancer Potential of Phenolic Compounds Isolated From Olive Oil", Eur J Cancer, Jun. 2000, 36(10), 1235-1247.
Palmer et al., "Pyrrolidine N-Oxides by Stereoselective Addition of Grignard and Lithium Compounds to 4,5-Dideoxy-2,3-O-isoprophylidene-d-erythro-4-pentenose N-Benzyl Nitrone and Subsequent Cope-House Cyclization", Eur. J. Org. Chem., Mar. 2001, 66(7), 1293-1308.
Paquette et al., "Evaluation of D-Ribose as an Enantiopure Building Block for Construction of the C-Ring of Taxol and its Congeners", J. Org. Chem., Dec. 1995, 60(24), 7849-7856.
Smith et al., "Synthesis and Assignment of Absolute Configuration of (−)—Oleocanthal: A Potent, Naturally Occurring Non-Steroidal Anti-Inflammatory and Anti-Oxidant Agent Derived From Extra Virgin Olive Oils", Organic Letters, Oct. 27, 2005, 7(22), 5075-5078.
Somanadhan et al., "Angiotensen Converting Enzyme (ACE) Inhibitors From Jasminum Azoricum and Jasminum Grandiflorum", Planta Medica, Apr. 1998, 64(3), 246-250.
Suzuki et al., "An Extremely Short Way to Prostaglandins", J. Am. Chem. Soc., (no month available) 1985, 107(11), 3348-3349.
Takenaka et al., "Nine New Secoiridoid Glucosides From Jasminum Nudiflorum", Chem. & Pharm. Bull, Mar. 2002, 50(3), 384-389.
Takenaka et al., "Secoiridoid and Iridoid Glucosides From Syringa Afghanica", Phytochemistry, Apr. 2002, 59(7), 779-787.
Weggen et al., "A Subset of NSAID's Lower Amyloidogenic Abeta42 Independently of Cyclooxygenase Activity", Nature, Nov. 8, 2001, 414(6860), 212-216.
Yang, "Preparation of Carbocyclic S-adenosylazamethionine Accompanied by a Practical Synthesis of (−)artisteromycin", J. Org. Chem., May 28, 2004, 69(11), 3993-3996.

* cited by examiner

USE OF THE IRRITATING PRINCIPAL OLEOCANTHAL IN OLIVE OIL, AS WELL AS STRUCTURALLY AND FUNCTIONALLY SIMILAR COMPOUNDS

REFERENCE TO GOVERNMENT GRANTS

This invention was made with government support under Grant Nos. NIH 29028 and NIH DC 00882 awarded by the National Institutes of Health. The government has certain rights in the invention.

CROSS-REFERENCE TO RELATED APPLICATIONS

This application is the National Stage of International Application No. PCT/US2007/067393, filed Apr. 25, 2007, the disclosure of which is incorporated herein by reference in its entirety.

FIELD OF THE INVENTION

The invention relates to the active principal in olive oil, termed oleocanthal and related analogs, and methods of using oleocanthals in various formulations including, food additives, pharmaceuticals, cosmetics, animal repellants, and discovery tools for mammalian irritation receptor genes, gene products, alleles, splice variants, alternate transcripts and the like.

BACKGROUND OF THE INVENTION

Over forty years ago, Fisher and Griffin suggested that the human oral cavity could be regarded as a pharmacological preparation in situ. They proposed that the perceived bitterness intensity of a compound reflects the compound's pharmacological activity and potency. As support for this idea, they pointed out that for several drugs, the active isomer was more bitter than the inactive one. There is also a rough correlation between the bitter potency of selected toxins and their $LD_{50}$ values.

In addition to the quality and intensity of a sensation, the perceived location may have pharmacological implications. Many compounds when put in the oral cavity elicit irritation (e.g., burning, stinging, cooling) and, just as for bitter taste, the irritation may serve as a signal of potential danger.

Some compounds with site-specific irritation have a beneficial effect. A desirable attribute of many premium olive oils is the distinctive irritation or pungency that is unusual because it is almost exclusively perceived on the pharynx and not in the mouth.

In 1993, Montedoro and co-workers reported the isolation of a new class of phenolic compounds (1-4), including the dialdehydic and aldehydic forms of ligstroside (5) and oleuropeine (6) from virgin olive oils (Montedoro, G. et al. (1993) *J. Agric. Food Chem.* 41:2228-2234) (See FIG. 1 for structures). These phenolic compounds comprise important minor constituents of virgin olive oils that have been implicated in the organoleptic characteristics including bitterness, pungency, and astringency (Andrewes, P. et al. (2003) *J. Agric. Food Chem.* 57:1415-1420). In addition, these agents have been suggested to contribute to the oxidative stability of virgin olive oil and as such are associated with health benefits of olive oils, specifically their antioxidant/anticancer activities (Owen, R. W. et al. (2000) *Food Chem. Toxicology* 38:647-659; Owen, R. W. et al. (2000) *Eur. J. Cancer* 36(10):1235-1247; Baldioli, M. et al. (1996) *J. Am. Oil Chem. Soc.* 73(11): 1589-1593; Manna, C. et al. (2002) *J. Agric. Food Chem.* 50(22):6521-6526). Similar structural features have been reported in the constituents of the *Jasminum* (Somanadhan, B. et al. (1998) *Planta Medica* 64:246-50; Takenaka, Y. et al. (2002) *Chem. & Pharm. Bull* 50(3):384-389) and related plant species (Takenaka, Y. et al. (2002) *Phytochemistry* 59(7):779-787). It has been shown that both ibuprofen and a Mediterranean diet (i.e., high in olive oil) both decrease the risk/incidence for breast and lung cancer.

In 2003, Busch and co-workers at Unilever Research and Development Vlaardingen (The Netherlands) identified deacetoxydialdehydic ligstroside aglycone as a principal contributor to the potent pungent (burning) sensation at the back of throat associated with high quality virgin olive oils (Andrewes, P. et al. (2003) *J. Agric. Food Chem.* 57:1415-1420). Studies at Firmenich, Inc., reached the same conclusion (Firmenich, Inc. study). The structure of 1 was assigned,

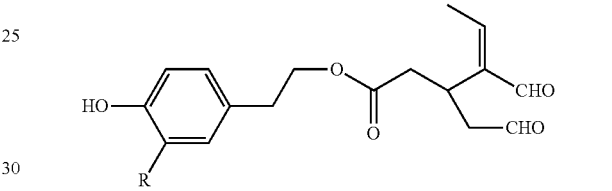

employing a series of 1 and 2D NMR experiments (Andrewes, P. et al. (2003) *J. Agric. Food Chem.* 57:1415-1420), in conjunction with comparison to literature data (Montedoro, G. et al. (1993) *J. Agric. Food Chem.* 41:2228-2234). The absolute stereochemistry remained undetermined. That 1 was responsible for the strong pungent (burning) sensation at the back of the throat was based on an extensive series of HPLC fraction analysis, omission analysis and correlation, and hydrolysis studies, in conjunction with human sensory studies. Andrewes et al., however, acknowledged that "a coelution compound causing the burning sensation" could not be eliminated without completing a synthesis of 1, which they stated to be "extremely challenging."

SUMMARY OF THE INVENTION

The invention provides the enantioselective total syntheses of both enantiomers of oleocanthal 1 (FIG. 1), which not only confirms the structure, but also permits the assignment of absolute stereochemistry of the olive oil irritant. The synthesis provides an effective route to both enantiomers for further biological/sensory evaluation. Studies demonstrate that the levorotary (−)-enantiomer of 1 (FIG. 1) is responsible for the organoleptic properties experienced with premium olive oils at back of the throat.

The invention therefore provides isolated and purified deacetoxydialdehydic ligstroside aglycone, which we term oleocanthal. The invention also provides functional derivatives of oleocanthal having the general formula I:

General Formula I

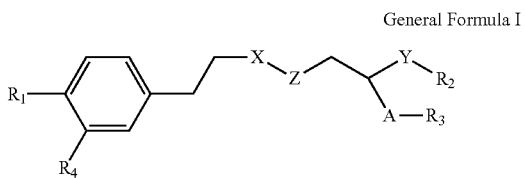

wherein:
R₁ and R₄ are independently H or OR₅,
R₂ and R₃ are independently CHO, or COOR₅
R₅ is a H, C₁-C₅ alkyl, or a glycoside
X is O, NH or CH₂
Y is C=CHCH₃, or CH—COOR₅
Z is C=O or CH—OR₅
A is CH₂, or CH—COOR₅.

The invention also provides analogs of oleocanthal having General Formula XII:

General Formula XII

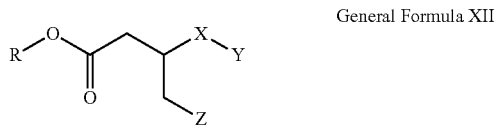

wherein:
R is CH₃, (CH₂)₂C₆H₄-4-OH, (CH₂)₃C₆H₄-4-OH, (CH₂) C₆H₄-4-OH, (CH₂)₃C₆H₄-4-X¹, (CH₂)₃C₆H₅, (CH₂)₃C₆H₄-2-OH, (CH₂)₃C₆H₄-3-OH, (CH₂)₃C₆H₃-3,4-OH, or (CH₂)₄CH₃;
X is C=CHCH₃ or CHCH₂CH₃;
X¹ is a halogen;
Y is CHO or CH₂OH; and
Z is CHO, CH₂OH, or Z and Y are CHOH (where Z and Y are connected by a single C—C bond).

The compounds of Formula I and XII, including oleocanthal, are collectively referred to herein as "oleocanthals" or "oleocanthal analogs" or "oleocanthal derivatives." The term "oleocanthal" specifically refers to deacetoxydialdehydic ligstroside aglycone.

The invention provides methods of synthesizing the purified enantiomers of oleocanthal.

The invention further provides methods of using oleocanthals in various formulations including, food additives (e.g., flavor enhancers, sweetness inhibitors, spices, flavorings, and preservatives); pharmaceuticals (e.g., antioxidants, micro-G protein and associated kinase inhibitors, Aβ42 inhibitors, presenilin modifiers, γ-secretase inhibitors, non-steroidal anti-inflammatories, anti-pyretics, cold and flu symptom relievers, Cox-1, Cox-2 inhibitors, Cox-3 inhibitors, lipoxygenase inhibitors, and wound healers); cosmetics; animal repellants; and discovery tools for mammalian irritation receptor genes, gene products, alleles, splice variants, alternate transcripts and the like.

DETAILED DESCRIPTION OF ILLUSTRATIVE EMBODIMENTS

Figure 1:
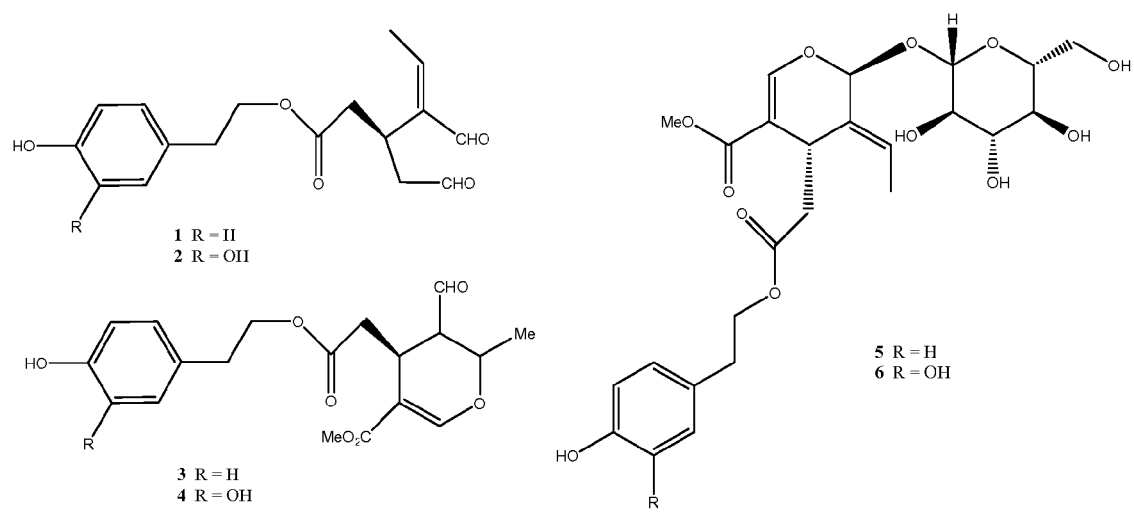
FIG. 1 shows phenolic compounds (1-4), including the dialdehydic and aldehydic forms of ligstroside (5) and oleuropeine (6).

The reference works, patents, patent applications, and scientific literature that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art. Any conflict between an art-understood definition of a word or phrase and a definition of the word or phrase as specifically taught in this specification shall be resolved in favor of the latter. Headings used herein are for convenience and are not to be construed as limiting.

Standard reference works setting forth the general principles of chemical synthesis are well known to those of skill in the art and include, for example, A. I. Vogel, VOGEL'S TEXTBOOK OF PRACTICAL ORGANIC CHEMISTRY (5ᵀᴴ EDITION) WILEY, N.Y. 1989; and ORGANIC SYNTHESES. 9 collective volumes; Index for vol. 1-8; Wiley, N.Y.

Standard reference works setting forth the general principles of recombinant DNA technology known to those of skill in the art include Ausubel et al., CURRENT PROTOCOLS IN MOLECULAR BIOLOGY, John Wiley & Sons, New York, 1998; Sambrook et al., MOLECULAR CLONING: A LABORATORY MANUAL, 2D ED., Cold Spring Harbor Laboratory Press, Plainview, N.Y., 1989; Kaufman et al., Eds., HANDBOOK OF MOLECULAR AND CELLULAR METHODS IN BIOLOGY AND MEDICINE, CRC Press, Boca Raton, 1995; McPherson, Ed., DIRECTED MUTAGENESIS: A PRACTICAL APPROACH, IRL Press, Oxford, 1991.

As used herein, "taste perception" refers to a response (e.g., biochemical, behavioral) or sensitivity to a taste stimulus. "Taste stimulus" as used herein refers to any compound that elicits, for example at the biochemical level (e.g., activation or inhibition of a taste receptor) or behavioral level (e.g., preference, indifference, or distaste), a taste response which would be perceived by a mammal as at least one of the five taste elements, including sweet, salty, sour, bitter, and umami. "Taste perception" or "taste stimulus," or variants thereof, does not require, though it does include, transmission of a neural signal resulting in in vivo sensation of taste by a mammal. Modification of taste perception includes an alteration of (enhancement of, reduction to, or change to) a biochemical response, an ingestive response, a taste preference, or general behavior of a mammal in response to a compound.

"Acyl" refers to a straight or branched alkyl-C=O group. "Thioacyl" refers to a straight or branched alkyl-C=S group. Preferred acyl and thioacyl groups are lower alkanoyl and lower thioalkanoyl having from 1 to about 6 carbon atoms in the alkyl group, and all combinations and subcombinations of ranges therein.

"Alkyl" refers to a saturated aliphatic hydrocarbon group which may be straight or branched and having from 1 to about 20 carbon atoms in the chain, and all combinations and subcombinations of ranges therein. Preferred alkyl groups may be straight or branched and have from 1 to about 10 carbon atoms in the chain. Branched means that a lower alkyl group such as, for example, methyl, ethyl or propyl, is attached to a linear alkyl chain.

"Lower alkyl" refers to an alkyl group having from 1 to about 6 carbons, and all combinations and subcombinations of ranges therein.

"Cycloalkyl" refers to an aliphatic ring having from about 3 to about 10 carbon atoms in the ring, and all combinations and subcombinations of ranges therein. Preferred cycloalkyl groups have from about 4 to about 7 carbon atoms in the ring.

"Carbamoyl" refers to an $H_2N$—C=O group. Alkylcarbamoyl and dialkylcarbamoyl means that the nitrogen of the carbamoyl is substituted by one or two alkyl groups, respectively.

"Carboxyl" refers to a COOH group.

"Alkoxy" refers to an alkyl-O group in which "alkyl" is as previously described. Lower alkoxy groups are preferred. Exemplary alkoxy groups include, for example, methoxy, ethoxy, n-propoxy, i-propoxy and n-butoxy.

"Alkoxyalkyl" refers to an alkyl group, as previously described, substituted by an alkoxy group, as previously described.

"Alkoxycarbonyl" refers to an alkoxy-C=O group.

"Aryl" refers to an aromatic carbocyclic radical containing from about 6 to about 10 carbons, and all combinations and subcombinations of ranges therein. Exemplary aryl groups include phenyl and naphthyl.

"Aralkyl" means an alkyl group substituted by an aryl radical. "Optionally substituted aralkyl" and "optionally substituted aryl" means that the aryl group, or the aryl group of the aralkyl group, may be substituted with one or more substituents which include, for example, alkyl, alkoxy, amino, nitro, carboxy, carboalkoxy, cyano, alkyl amino, halo, hydroxy, hydroxyalkyl, mercaptyl, alkylmercaptyl, trihaloalkyl, carboxyalkyl or carbamoyl.

"Aralkoxycarbonyl" refers to an aralkyl-O—C=O group.

"Aryloxycarbonyl" refers to an aryl-O—C=O group.

"Carbalkoxy" refers to a carboxyl substituent esterified with an alcohol of the formula $C_nH_{2n+1}OH$, wherein n is from 1 to about 6.

"Halogen" (or "halo") refers to chlorine (chloro), fluorine (fluoro), bromine (bromo) or iodine (iodo). Preferred among the halogens (or halos) are fluorine (or fluoro) and chlorine (or chloro), and most preferably fluorine.

"Heterocyclyl" refers to a ring structure containing from about 4 to about 10 members in which one or more of the atoms in the ring is an element other than carbon, e.g., N, O or S. Heterocyclyl groups may be aromatic or non-aromatic, i.e., the rings may be saturated, partially unsaturated, or fully unsaturated. Preferred heterocyclyl groups include, for example, pyridyl, pyridazinyl, pyrimidinyl, isoquinolinyl, quinolinyl, quinazolinyl, imidazolyl, pyrrolyl, furanyl, thienyl, thiazolyl, benzothiazolyl, piperidinyl, pyrrolidinyl, tetrahydrofuranyl, tetrahydropyranyl, and morphonlinyl groups.

"Optionally substituted heterocyclyl" means that the heterocyclyl group may be substituted by one or more substituents wherein the substituents include, for example, alkoxy, alkylamino, aryl, carbalkoxy, carbamoyl, cyano, halo, heterocyclyl, trihalomethyl, hydroxy, mercaptyl, alkylmercaptyl and nitro.

"Hydroxyalkyl" refers to an alkyl group substituted by a hydroxy group. Hydroxy lower alkyl groups are preferred. Exemplary preferred groups include, for example, hydroxymethyl, 2-hydroxyethyl, 2-hydroxypropyl and 3-hydroxypropyl.

"Hydrogenation catalyst" refers to any compounds known in the art of organic synthesis to facilitate the addition of hydrogen. Hydrogenation catalysts include, but are not limited to palladium on carbon, palladium hydroxide on carbon, palladium on calcium carbonate poisoned with lead, and platinum on carbon.

"Sulfonating agent" refers to any reagents known in the art of organic synthesis to react with an alcohol to provide a sulfonate ester. Examples include, but are not limited to methanesulfonyl chloride, methanesulfonic anhydride, trifluoromethane sulfonyl chloride, trifluoromethane sulfonic anhydride, benzene sulfonyl chloride, p-toluenesulfonyl chloride, a p-toluenesulfonyl anhydride. "Sulfonate ester" includes groups which result when a sulfonating agent is reacted with an alcohol in the presence of an acid scavenger to give a compound of form —OA, wherein A is $SO_2R'$, with R' deriving from the sulfonating agent.

"Reducing agent" refers to any reagents known in the art of organic synthesis to reduce the oxidation state of a carbon atom, for example, by reducing a ketone to an alcohol. Reducing agents include, but are not limited to hydride derivatives, such as borohydrides, including lithium borohydride and sodium borohydrides.

"Methylating agent" refers to any reagent known in the art of organic synthesis to donate a methyl group to an alcohol to form an ether. Methylating agents include, but are not limited to methylhalides such as methyliodide, methylchloride, methylbromide, and dimethylsulfate.

"Acid scavenger" refers to any species known in the art of organic synthesis capable of accepting a proton without reacting with the starting material or product.

"Concatenated" refers to multi-step processes (i.e., processes containing two or more steps) wherein the steps may be performed in a substantially continuous or sequential manner, preferably without the necessity for interim isolation and/or purification of the intermediate compounds.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound which has been prepared by the addition of an acid. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds may exist as zwitterions. All forms of the compounds, including free acid, free base and zwitterions, are contemplated to be within the scope of the present invention.

The reactions of the synthetic methods described and claimed herein may be carried out in suitable solvents which may be readily selected by one skilled in the art of organic synthesis. Generally, suitable solvents are solvents which are substantially non-reactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction, suitable solvents for a particular work-up following the reaction may be selected. Suitable solvents, as used herein may include, by way of example and without limitation, chlorinated solvents, hydrocarbon solvents, aromatic solvents, ether solvents, protic solvents, polar aprotic solvents, and mixtures thereof.

Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluoroethane and hexafluoroethane.

Suitable hydrocarbon solvents include, but are not limited to alkane or aromatic solvents such as cyclohexane, pentane, hexane, toluene, cycloheptane, methylcyclohexane, heptane, ethylbenzene, m-, o-, or p-xylene, octane, indane, nonane, benzene, ethylbenzene, and m-, o-, or p-xylene.

Suitable ether solvents include, but are not limited to dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, or t-butyl methyl ether.

Suitable protic solvents include, but are not limited to water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide (DMSO), propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, and hexamethylphosphoramide.

The term "substantially pure form," as used herein, means that the compounds prepared using the present processes may preferably be substantially devoid of organic impurities. The term "organic impurities," as used herein, refers to organic materials, compounds, etc., other than the desired product, that may be typically associated with synthetic organic chemical transformations including, for example, unreacted starting reagents, unreacted intermediate compounds, and the like. In preferred form, the present processes may provide compounds that are at least about 75% pure, as measured by standard analytical techniques such as, for example, HPLC. Preferably, the compounds prepared using the present processes may be at least about 80% pure, with a purity of at least about 85% being more preferred. Even more preferably, the compounds prepared using the present processes may be at least about 90% pure, with a purity of at least about 95% being more preferred. In particularly preferred embodiments, the compounds prepared using the present processes may be more than about 95% pure, with a purity of about 100% being especially preferred.

Typically, substituted chemical moieties include one or more substituents that replace hydrogen. Exemplary substituents include, for example, halo (e.g., F, Cl, Br, I), alkyl, alkenyl, alkynyl, aralkyl, aryl, heteroaryl, heterocyclyl, hydroxyl (OH), nitro ($NO_2$), nitrosyl (NO), cyano (CN), cyanato (CNO), thiocyanato (SCN), amino (e.g., $NH_2$, NHR', $NR'_2$), azido ($N_3$), carboxyl (COOH), C(O)R', OR', C(O)OR', NHC(O)R', aminocarbonyl, thiol, thiolato (SR'), sulfonic acid ($SO_3H$), phosphonic acid ($PO_3H$), $SO_2R'$, phosphino ($PH_2$, PHR', $PR'_2$), silyl ($SiR'_3$, $SiHR'_2$, $SiH_2R'$, $SiH_3$) and the like. In relation to the aforementioned substituents, each moiety R' can be, independently, any of H, alkyl, aryl, aralkyl, heteroaryl, or heterocyclyl, for example.

Processes of the present invention may yield mixtures of diastereomers. Thus, in some embodiments, processes may, if desired, include a separation step to isolate diastereomers. Methods for separation of diastereomers are well known in the art and include, for example, chiral column chromatography, HPLC, re-crystallization, or classical resolution methods involving selective reactivity. In some embodiments, asymmetric synthesis may be used to produce a specific diastereomer.

As used herein "polynucleotide" refers to a nucleic acid molecule and includes genomic DNA, cDNA, RNA, mRNA, mixed polymers, recombinant nucleic acids, fragments and variants thereof, and the like. Polynucleotide fragments of the invention comprise at least 10, and preferably at least 12, 14, 16, 18, 20, 25, 30, 35, 40, 45, 50, 75, or 100 consecutive nucleotides of a reference polynucleotide. The polynucleotides include sense and antisense strands. The polynucleotides may be naturally occurring or non-naturally occurring polynucleotides. A "synthesized polynucleotide" as used herein refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means. The polynucleotides of the invention may be single- or double-stranded. The polynucleotides of the invention may be chemically modified and may contain non-natural or derivatized nucleotide bases as will be readily appreciated by those skilled in the art. Such modifications include, for example, labels, methylation, substitution of one or more nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides, etc.), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

"Recombinant nucleic acid" is a nucleic acid generated by combination of two segments of nucleotide sequence. The combination may be, for example, by chemical means or by genetic engineering.

As used herein, "polynucleotide amplification" refers to a broad range of techniques for increasing the number of copies of specific polynucleotide sequences. Typically, amplification of either or both strand(s) of the target nucleic acid comprises the use of one or more nucleic acid-modifying enzymes, such as a DNA polymerase, ligase, RNA polymerase, or RNA-dependent reverse transcriptase. Examples of polynucleotide amplification include, but are not limited to, polymerase chain reaction (PCR), nucleic acid sequence based amplification (NASB), self-sustained sequence replication (3SR), strand displacement activation (SDA), ligase chain reaction, Qβ replicase system, and the like. A wide variety of alternative cloning and in vitro amplification methodologies are well known to those skilled in the art. Examples of these techniques are found in, for example, Berger et al., Guide to Molecular Cloning Techniques, METHODS IN ENZYMOLOGY 152, Academic Press, Inc., San Diego, Calif. (Berger), which is incorporated herein by reference in its entirety.

As used herein, the term "oligonucleotide" or "primer" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar, or complementary DNA or RNA in a particular cell or tissue. Oligonucleotides comprise portions of a nucleic acid sequence having at least about 10 nucleotides and as many as about 50 nucleotides, often about 12 or 15 to about 30 nucleotides. They are chemically synthesized and may be used as probes. "Primer pair" refers to a set of primers including a 5' upstream primer that hybridizes with the 5' end of a target sequence to be amplified and a 3' downstream primer that hybridizes with the complement of the 3' end of the target sequence to be amplified.

As used herein, the term "probe" refers to nucleic acid sequences of variable length, for example between at least about 10 and as many as about 8,500 nucleotides, depending on use. Probes are used in the detection of identical, similar, or complementary target nucleic acid sequences, which target sequences may be single- or double-stranded. Longer probes are usually obtained from a natural or recombinant source, are highly specific, and are much slower to hybridize than oligomers, or shorter probes. They may be single- or double-stranded and are carefully designed to have specificity in PCR, hybridization membrane-based, or ELISA-like technologies.

As used herein, the phrase "stringent hybridization conditions" or "stringent conditions" refers to conditions under which a probe, primer, or oligonucleotide will hybridize to its target sequence, but to a minimal number of or no other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are hybridized to their complements at equilibrium. Stringent temperature conditions will generally include temperatures in excess of 30° C., typically in excess of 37° C., and may be in excess of 45° C. Stringent salt conditions will ordinarily be less than 1.0 M, typically less than 0.5 M, and may be less than 0.2 M. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers, or oligonucleotides (e.g., 10 to 50 nucleotides) and at least about 60° C. for longer probes, primers, or oligonucleotides. Stringent conditions may also be achieved with the addition of destabilizing agents, such as formamide.

As used herein "antisense oligonucleotide" refers to a nucleic acid molecule that is complementary to at least a portion of a target nucleotide sequence of interest and specifically hybridizes to the target nucleotide sequence under physiological conditions. The term "double stranded RNA" or "dsRNA" as used herein refers to a double-stranded RNA molecule capable of RNA interference, including small interfering RNA (siRNA) (see for example, Bass (2001) Nature 411:428-429; Elbashir et al. (2001) Nature, 411:494-498).

As used herein, the term "complementary" refers to Watson-Crick base pairing between nucleotide units of a nucleic acid molecule.

The term "marker gene" or "reporter gene" refers to a gene encoding a product that, when expressed, confers a phenotype at the physical, morphologic, or biochemical level on a transformed cell that is easily identifiable, either directly or indirectly, by standard techniques and includes, but is not limited to, genes encoding proteins that confer resistance to toxins or antibiotics such as ampicillin, neomycin, and methotrexate; genes encoding proteins that complement auxotrophic deficiencies; and genes encoding proteins that supply critical components not available from complex media. Examples of marker genes include green fluorescent protein (GFP), red fluorescent protein (DsRed), alkaline phosphatase (AP), β-lactamase, chloramphenicol acetyltransferase (CAT), adenosine deaminase (ADA), aminoglycoside phosphotransferase (NEOr, G418r) dihydrofolate reductase (DHFR), hygromycin-B-phosphotransferase (HPH), thymidine kinase (TK), lacZ (encoding β-galactosidase), β-lactamase, luciferase (luc), and xanthine guanine phosphoribosyltransferase (XGPRT). As with many of the standard procedures associated with the practice of the invention, skilled artisans will be aware of additional sequences that can serve the function of a marker or reporter. Thus, this list is merely meant to show examples of what can be used and is not meant to limit the invention.

As used herein, the term "promoter" refers to a regulatory element that regulates, controls, or drives expression of a nucleic acid molecule of interest and can be derived from sources such as from adenovirus, SV40, parvoviruses, vaccinia virus, cytomegalovirus, or mammalian genomic DNA. Examples of suitable promoters include, but are not limited to, CMV, MSH2, trp, lac, phage, and TRNA promoters. Suitable promoters that can be used in yeast include, but are not limited to, such constitutive promoters as 3-phosphoglycerate kinase and various other glycolytic enzyme gene promoters such as enolase or glyceraldehydes-3-phosphate dehydrogenase, or such inducible promoters as the alcohol dehydrogenase 2 promoter or metallothionine promoter. Again, as with many of the standard procedures associated with the practice of the invention, skilled artisans will be aware of additional promoters that can serve the function of directing the expression of a marker or reporter. Thus, the list is merely meant to show examples of what can be used and is not meant to limit the invention.

"Operably linked" refers to juxtaposition wherein the components are in a functional relationship. For example, a promoter is operably linked or connected to a coding sequence if it controls the transcription or expression of the sequence.

The terms "polypeptide," "peptide," and "protein" are used interchangeably herein. "Polypeptide" refers to a polymer of amino acids without referring to a specific length. Polypeptides of the invention include peptide fragments, derivatives, and fusion proteins. Peptide fragments preferably have at least about 10, 15, 20, 25, 30, 35, 40, 45, 50, 60, 70, 80, 90, or 100 amino acids. Some peptide fragments of the invention are biologically active. Biological activities include immunogenicity, ligand binding, and activity associated with the reference peptide. Immunogenic peptides and fragments of the invention generate an epitope-specific immune response, wherein "epitope" refers to an immunogenic determinant of a peptide and preferably contains at least three, five, eight, nine, ten, fifteen, twenty, thirty, forty, forty-five, or fifty amino acids. Some immunogenic peptides of the invention generate an immune response specific to that peptide. Polypeptides of the invention include naturally occurring and non-naturally occurring peptides. The term includes modified polypeptides (wherein examples of such modifications include glycosylation, acetylation, phosphorylation, carboxylation, ubiquitination, labeling, etc.), analogs (such as non-naturally occurring amino acids, substituted linkages, etc.), and functional mimetics. A variety of methods for labeling polypeptides are well known in the art and include radioactive isotopes such as $^{32}P$ or $^{35}S$, ligands that bind to labeled antiligands (e.g., antibodies), fluorophores, chemiluminescent agents, enzymes, and antiligands.

As used herein, the term "amino acid" denotes a molecule containing both an amino group and a carboxyl group. In some embodiments, the amino acids are $\alpha$-, $\beta$-, $\gamma$- or $\delta$-amino acids, including their stereoisomers and racemates. As used herein the term "L-amino acid" denotes an $\alpha$-amino acid having the L configuration around the $\alpha$-carbon, that is, a carboxylic acid of general formula CH(COOH)(NH$_2$)-(side chain), having the L-configuration. The term "D-amino acid" similarly denotes a carboxylic acid of general formula CH(COOH)(NH$_2$)-(side chain), having the D-configuration around the $\alpha$-carbon. Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. Amino acid substituents may be attached, for example, through their carbonyl groups through the oxygen or carbonyl carbon thereof, or through their amino groups, or through functionalities residing on their side chain portions.

The amino acid sequences are presented in the amino (N) to carboxy (C) direction, from left to right. The N-terminal $\alpha$-amino group and the C-terminal $\beta$-carboxy groups are not depicted in the sequence. The nucleotide sequences are presented by single strands only, in the 5' to 3' direction, from left to right. Nucleotides and amino acids are represented in the manner recommended by the IUPAC-IUB Biochemical Nomenclature Commission, or amino acids are represented by their three letters code designations.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates. Binding may be detected in many different manners. As a non-limiting example, the physical binding interaction between two molecules can be detected using a labeled compound. Other methods of detecting binding are well-known to those of skill in the art.

As used herein, the term "contacting" means bringing together, either directly or indirectly, a compound into physical proximity to a molecule of interest. Contacting may occur, for example, in any number of buffers, salts, solutions, or in a cell or cell extract.

As used herein, the terms "modulates" or "modifies" means an increase or decrease in the amount, quality, or effect of a particular activity or protein. "Modulators" refer to any inhibitory or activating molecules identified using in vitro and in vivo assays for, e.g., agonists, antagonists, and their homologues, including fragments, variants, and mimetics, as defined herein, that exert substantially the same biological activity as the molecule "Inhibitors" or "antagonists" are modulating compounds that reduce, decrease, block, prevent, delay activation, inactivate, desensitize, or downregulate the biological activity or expression of a molecule or pathway of interest. "Inducers," "activators," or "agonists" are modulating compounds that increase, induce, stimulate, open, activate, facilitate, enhance activation, sensitize, or upregulate a molecule or pathway of interest. In some preferred embodiments of the invention, the level of inhibition or upregulation of the expression or biological activity of a molecule or pathway of interest refers to a decrease (inhibition or downregulation) or increase (upregulation) of greater than about 50%, 60%, 70%, 75%, 80%, 85%, 90%, 91%, 92%, 93%, 94%, 95%, 96%, 97%, 98%, or 99%. The inhibition or upregulation may be direct, i.e., operate on the molecule or pathway of interest itself, or indirect, i.e., operate on a molecule or pathway that affects the molecule or pathway of interest.

A "purified" or "substantially purified" polynucleotide or polypeptide is substantially separated from other cellular components that naturally accompany a native (or wild-type) nucleic acid or polypeptide and/or from other impurities (e.g., agarose gel). A purified polypeptide or protein will comprise about 60% to more than 99% w/w of a sample, and may be about 90%, about 95%, or about 98% pure. As used herein, the term "isolated" refers to a molecule that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

"About" as used herein refers to +/−10% of the reference value.

As used herein, "variant" nucleotide or amino acid sequences refer to homologues, including, for example, isoforms, species variants, allelic variants, and fragments of the sequence of interest. "Homologous nucleotide sequence" or "homologous amino acid sequence," or variations thereof, refers to sequences characterized by a relative identity, at the nucleotide level with respect to a reference sequence, or homology at the amino acid level, of at least about 60%, at least about 70%, at least about 75%, at least about 80%, at least about 81%, at least about 82%, at least about 83%, at least about 84%, at least about 85%, preferably at least about 90%, at least about 95%, at least about 98%, or at least about 99%, and more preferably 100%, to a reference sequence, or portion or fragment thereof encoding or having a functional domain.

As is well known in the art, because of the degeneracy of the genetic code, there are numerous DNA and RNA molecules that can code for the same polypeptide as that encoded by a nucleotide sequence of interest. The present invention, therefore, contemplates those other DNA and RNA molecules which, on expression, encode a polypeptide encoded by the nucleic acid molecule of interest. DNA and RNA molecules other than those specifically disclosed herein characterized simply by a change in a codon for a particular amino acid, are within the scope of this invention.

Amino acid "insertions," "substitutions" or "deletions" are changes to or within an amino acid sequence. The variation allowed in a particular amino acid sequence may be experimentally determined by producing the peptide synthetically or by systematically making insertions, deletions, or substitutions of nucleotides in the nucleic acid sequence using recombinant DNA techniques. Alterations of the naturally occurring amino acid sequence can be accomplished by any of a number of known techniques. For example, mutations can be introduced into the polynucleotide encoding a polypeptide at particular locations by procedures well known to the skilled artisan, such as oligonucleotide-directed mutagenesis.

A chemical variant of the present invention may exhibit substantially the biological activity of a naturally occurring oleocanthal, or have improved activity. "Biological activity" as used herein refers to the level of a particular function (for example, antioxidant activity, anti-inflammatory activity, etc.) of a molecule or pathway of interest in a biological system. "Wild-type biological activity" refers to the normal level of function of a molecule or pathway of interest. "Reduced biological activity" refers to a decreased level of function of a molecule or pathway of interest relative to a reference level of biological activity of that molecule or pathway. "Increased biological activity" refers to an increased level of function of a molecule or pathway of interest relative to a reference level of biological activity of that molecule or pathway. For example, increased biological activity may refer to an increased level of biological activity relative to the wild-type biological activity of a molecule or pathway of interest. Reference to exhibiting "substantially the biological activity of naturally-occurring oleocanthal" indicates that variants within the scope of the invention can comprise substitutions, meaning that one or more chemical moieties of oleocanthal are replaced by different chemical moieties and such compounds retain the biological activity of oleocanthal, have substantially the same biological activities of oleocanthal, or have improved biological activity as compared to naturally-occurring oleocanthal.

A nucleotide and/or amino acid sequence of a nucleic acid molecule or polypeptide identified by the screening method of the invention may be used to search a nucleotide and amino acid sequence databank for regions of similarity using Gapped BLAST (Altschul, et al. (1997) *Nucl. Acids Res.* 25:3389). Briefly, the BLAST algorithm, which stands for Basic Local Alignment Search Tool is suitable for determining sequence similarity (Altschul, et al. (1990) *J. Mol. Biol.* 215:403-410). Software or performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul, et al. (1990) *J. Mol. Biol.* 215:403-410). These initial neighborhood word hits act as seeds for initiating searches to find HSPs containing them. The word hits are extended in both directions along each sequence for as far as the cumulative alignment score can be increased. Extension for the word hits in each direction are halted when: (1) the cumulative alignment score falls off by the quantity X from its maximum achieved value; (2) the cumulative score goes to zero or below, due to the accumulation of one or more negative-scoring residue alignments; or (3) the end of either sequence is reached. The BLAST algorithm parameters W, T, and X determine the sensitivity and speed of the alignment. The BLAST program uses as defaults a word length (W) of 11, the BLOSUM62 scoring matrix (Henikoff, et al. (1992) *Proc. Natl. Acad. Sci. USA* 89:10915-10919) alignments (B) of 50, expectation (E) of 10, M=5, N=4, and a comparison of both strands. The BLAST algorithm (Karlin, et al. (1993) *Proc. Natl. Acad. Sci. USA* 90:5873-5877) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a gene or cDNA if the smallest sum probability in comparison of the test nucleic acid to the reference nucleic acid is less than about 1, preferably less than about 0.1, more preferably less than about 0.01, and most preferably less than about 0.001.

The term "mimetic" as used herein refers to a compound that is sterically similar to a reference compound. Mimetics are structural and functional equivalents to the reference compounds.

The terms "patient" and "subject" are used interchangeably herein and include, but are not limited to amphibians, birds, dogs, cats, cattle, horses, buffalo, llama, sheep, goats, pigs, rodents, monkeys, apes, and humans. "Host cell" includes, for example, prokaryotic cells, such as bacterial cells; eukaryotic cells, such as yeast cells and animal cells, including, but not limited to invertebrate cells (e.g., insect cells and nematode cells), amphibian cells (e.g., frog cells), particularly mammalian cells (e.g., human, rodent, canine, feline, caprine, ovine, bovine, equine, porcine, simian); or plant cells. "Rodents" include, for example, rats and mice. Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), N1E-115 (Liles et al., (1986) *J.*

Biol. Chem. 261:5307-5313), PC 12 human hepatocellular carcinoma cells (e.g., Hep G2).

The term "treatment" as used herein refers to any indicia of success of prevention, treatment, or amelioration of a disease or condition. Treatment includes any objective or subjective parameter, such as, but not limited to, abatement, remission, normalization of receptor activity, reduction in the number or severity of symptoms or side effects, or slowing of the rate of degeneration or decline of the patient. Treatment also includes a prevention of the onset of symptoms in a patient that may be at increased risk for or is suspected of having a disease or condition but does not yet experience or exhibit symptoms thereof.

As used herein, the term "compound" means any identifiable chemical or molecule, including, but not limited to a small molecule, peptide, protein, sugar, nucleotide, or nucleic acid. Such compound can be natural or synthetic.

As used herein, "bitter" refers to a basic taste characterized by solutions of such compounds as quinine, caffeine, and certain other alkaloids, that are sensed in humans primarily by taste buds at the back of the tongue, which are perceived as acrid, sharp, pungent, or harsh.

As used herein, "sweet" refers to a basic taste characterized by solutions of sugars (e.g., sucrose and glucose), alcohols, glycols, some small molecules and some amino acids that are sensed in humans primarily by taste buds on the tip of the tongue, which are perceived as agreeable or pleasing.

As used herein, "sour" refers to a basic taste characterized by solutions of vinegar and the juices of most unripe fruits and having a acid or sharp, tart, or biting taste.

Oleocanthals of the invention have the general formula I or XII. Compounds of general formula I have the following structure:

General Formula I

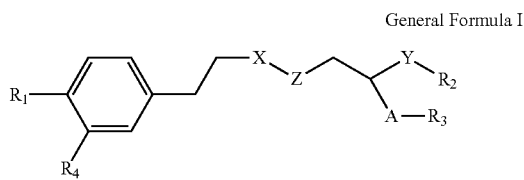

wherein:
$R_1$ and $R_4$ are independently H or $OR_5$
$R_2$ and $R_3$ are independently CHO, or $COOR_5$
$R_5$ is a H, $C_1$-$C_5$ alkyl, or a glycoside
X is O, NH or $CH_2$
Y is C=$CHCH_3$, or CH—$COOR_5$
Z is C=O or CH—$OR_5$
A is $CH_2$, or CH—$COOR_5$.

Compounds of general formula XII have the following structure:

General Formula XII

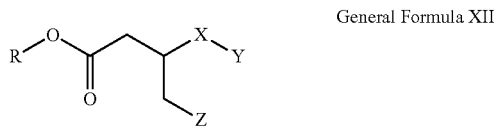

wherein:
R is $CH_3$, $(CH_2)_2C_6H_4$-4-OH, $(CH_2)_3C_6H_4$-4-OH, $(CH_2)C_6H_4$-4-OH, $(CH_2)_3C_6H_4$-4-$X^1$, $(CH_2)_3C_6H_5$, $(CH_2)_3C_6H_4$-2-OH, $(CH_2)_3C_6H_4$-3-OH, $(CH_2)_3C_6H_3$-3,4-OH, or $(CH_2)_4CH_3$;

X is C=$CHCH_3$ or $CHCH_2CH_3$;
$X^1$ is a halogen;
Y is CHO or $CH_2OH$; and
Z is CHO, $CH_2OH$, or Z and Y are CHOH (where Z and Y are connected by a single C—C bond).

"Oleocanthal" is specifically deacetoxydialdehydic ligstroside aglycone, which exists as a single isomer (enantiomer). The (−)-enantiomer is the natural product and has the following chemical formula:

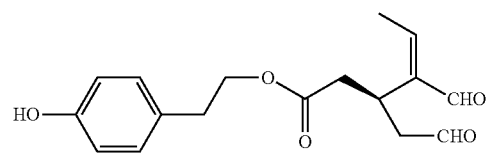

The enantiomers of oleocanthal may be synthesized and purified by the following methods:

(−)-Oleocanthal:

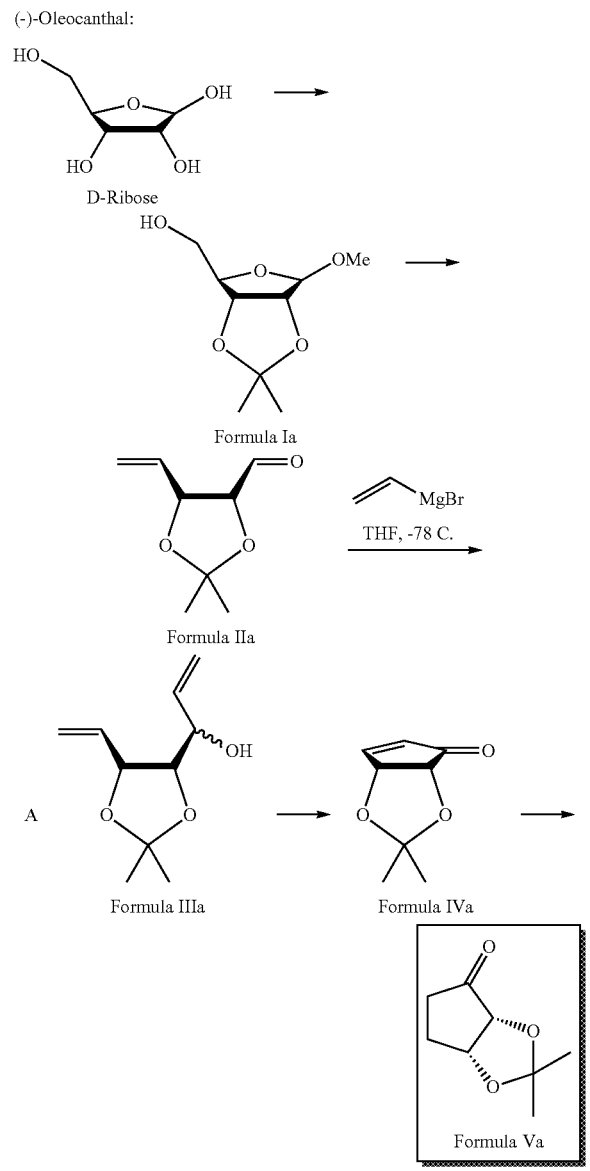

-continued

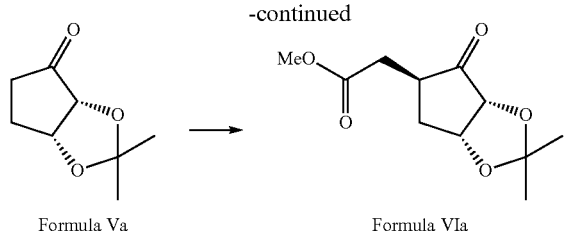

Formula Va  Formula VIa

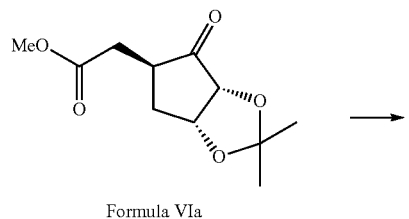

Formula VIa

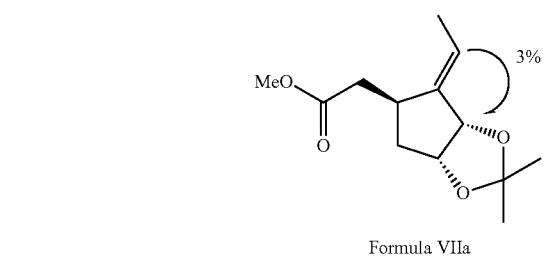

Formula VIIa

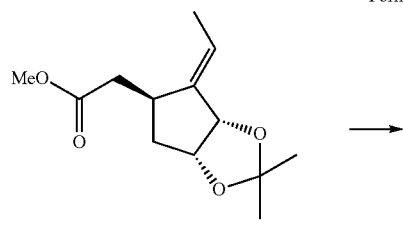

Formula VIIa

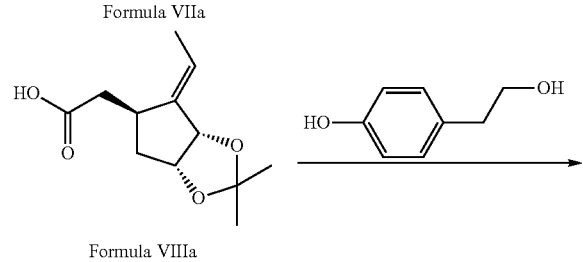

Formula VIIIa

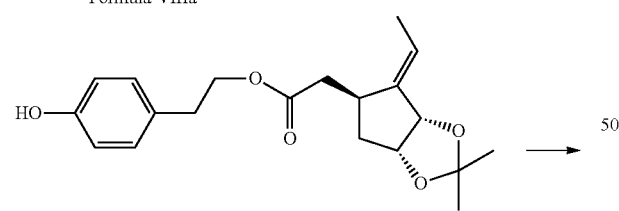

Formula IXa

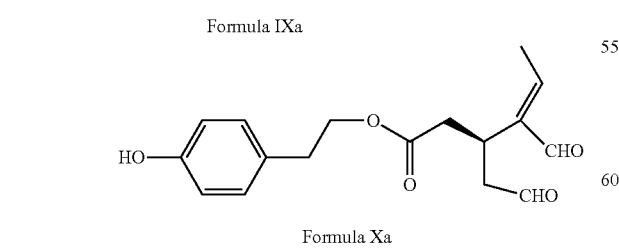

Formula Xa

Figure 3:
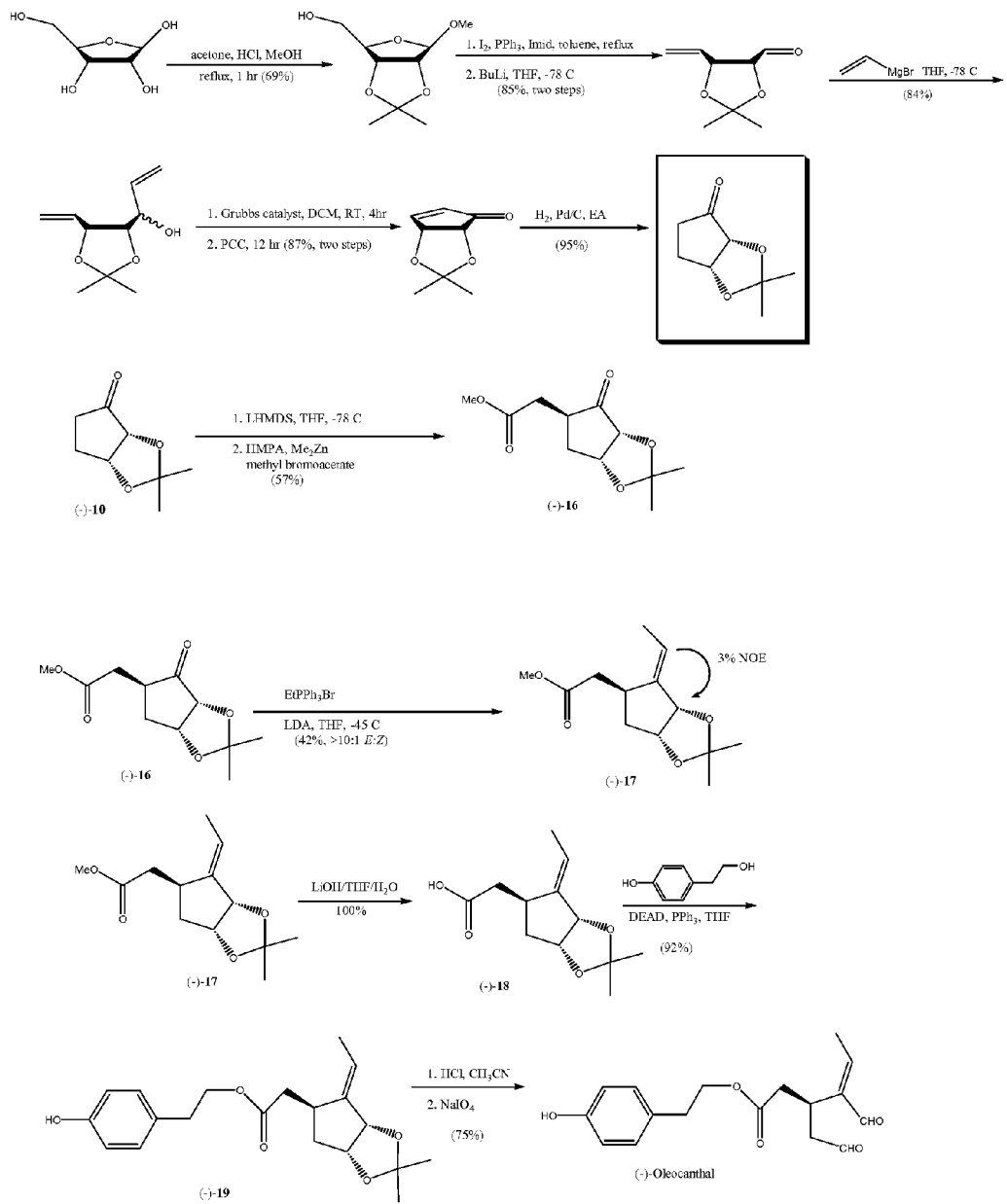
FIG. 3 shows the synthetic scheme of (−)-oleocanthal.

D-ribose may be converted to Formula I with a strong acid (e.g., hydrochloric acid) in acetone and methanol to yield Formula Ia. The compound of Formula Ia may be treated with a halogenation reagent (e.g., iodine), phosphine (PPh₃) imidazole followed by metal halogen exchange (e.g., BuLi or Zn) induced ring opening to yield an aldehyde of Formula IIa. Thereafter the compound of Formula IIa may be contacted with a CH₂=CH—MgBr in a suitable solvent (e.g., tetrahydrofuran) to yield a compound of Formula IIIa which is converted to a compound of Formula IVa by treatment with Grubbs catalyst in a suitable solvent (e.g., dichloromethane (DCM)) followed by treatment with an oxidizing reagent (e.g., pyridinium chlorochromate (PCC)). The compound of Formula IVa is contacted with hydrogen, palladium in a suitable solvent (e.g., ethyl acetate (EtOAc)) to yield (–)-cyclopentanone (Formula Va). The (–)-cyclopentanone (Formula Va) is treated with lithium hexamethyldisilazide (LHMDS) followed by hexamethylphosphoramide (HMPA), dimethyl zinc and alkyl bromoacetate (e.g., methyl, ethyl, tert-butyl) to yield (–)-(3,4-dimethoxy-2-oxo-cyclopentyl)-acetic acid ester (Formula VIa). The compound of Formula VIa is subjected to a Wittig ethylnation using ethyltriphenylphosphine bromide (or iodide) at reduced temperature, preferably –40° C. or less. The ester is hydrolyzed (Formula VIIIa) and the compound of formula VIIIa is contacted with 4-hydroxyphenethyl alcohol in the presence of phosphine, dialkyl azodicarboxylate (e.g., diethyl or diisopropyl) (DEAD or DIAD) to give Formula IXa. The vicinal diol moiety is liberated and oxidative cleavage yields the (–)-oleocanthal (Formula Xa). See also FIG. 3.

(+)-Oleocanthal:

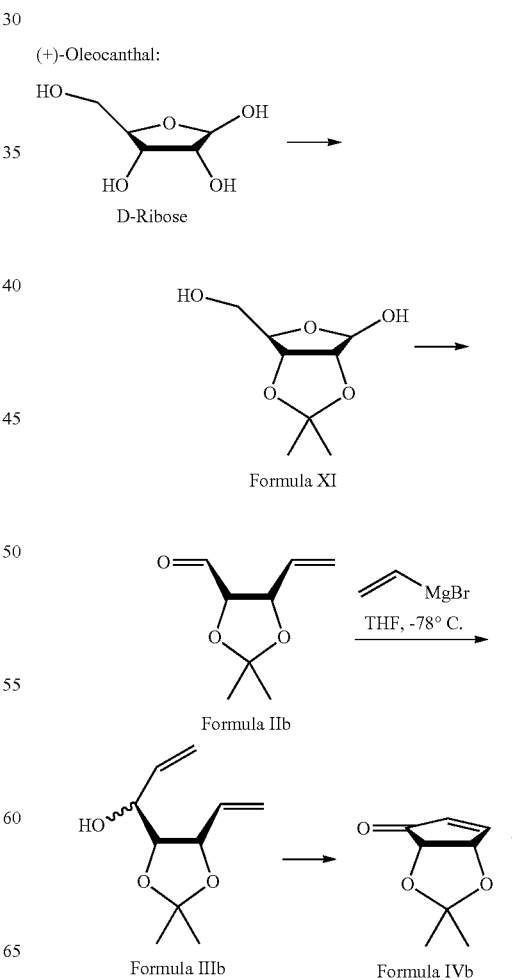

D-Ribose

Formula XI

Formula IIb

Formula IIIb  Formula IVb

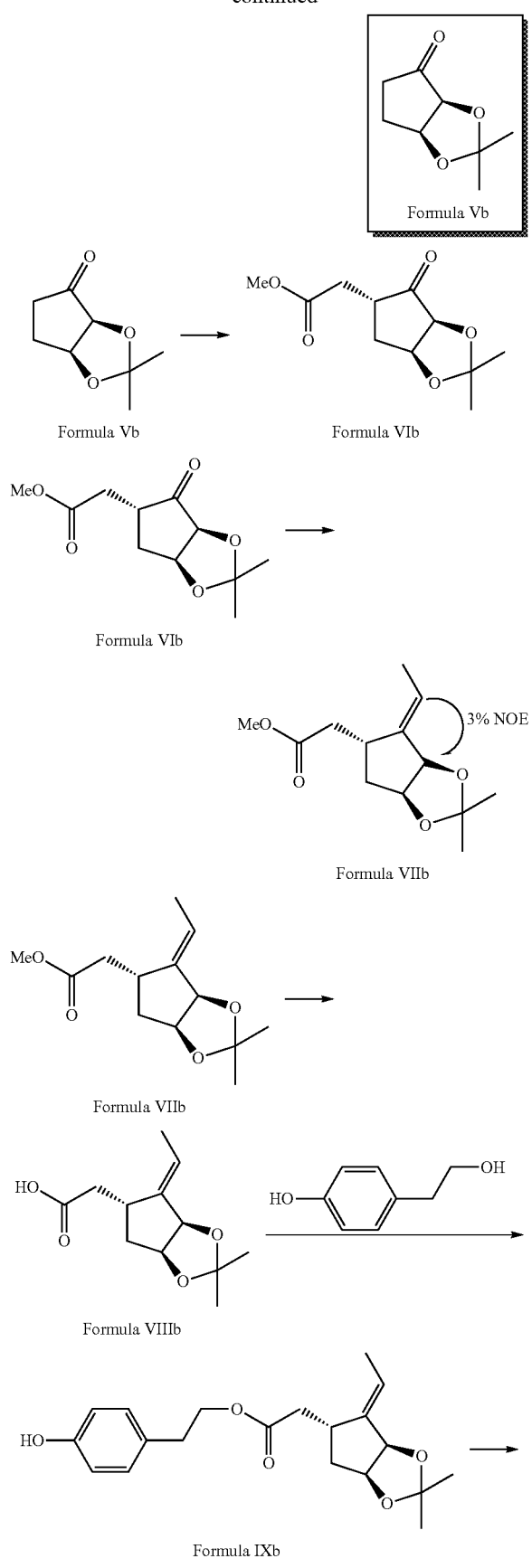
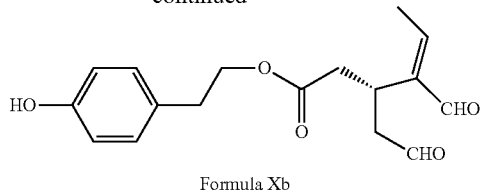

Formula Xb

Figure 4:
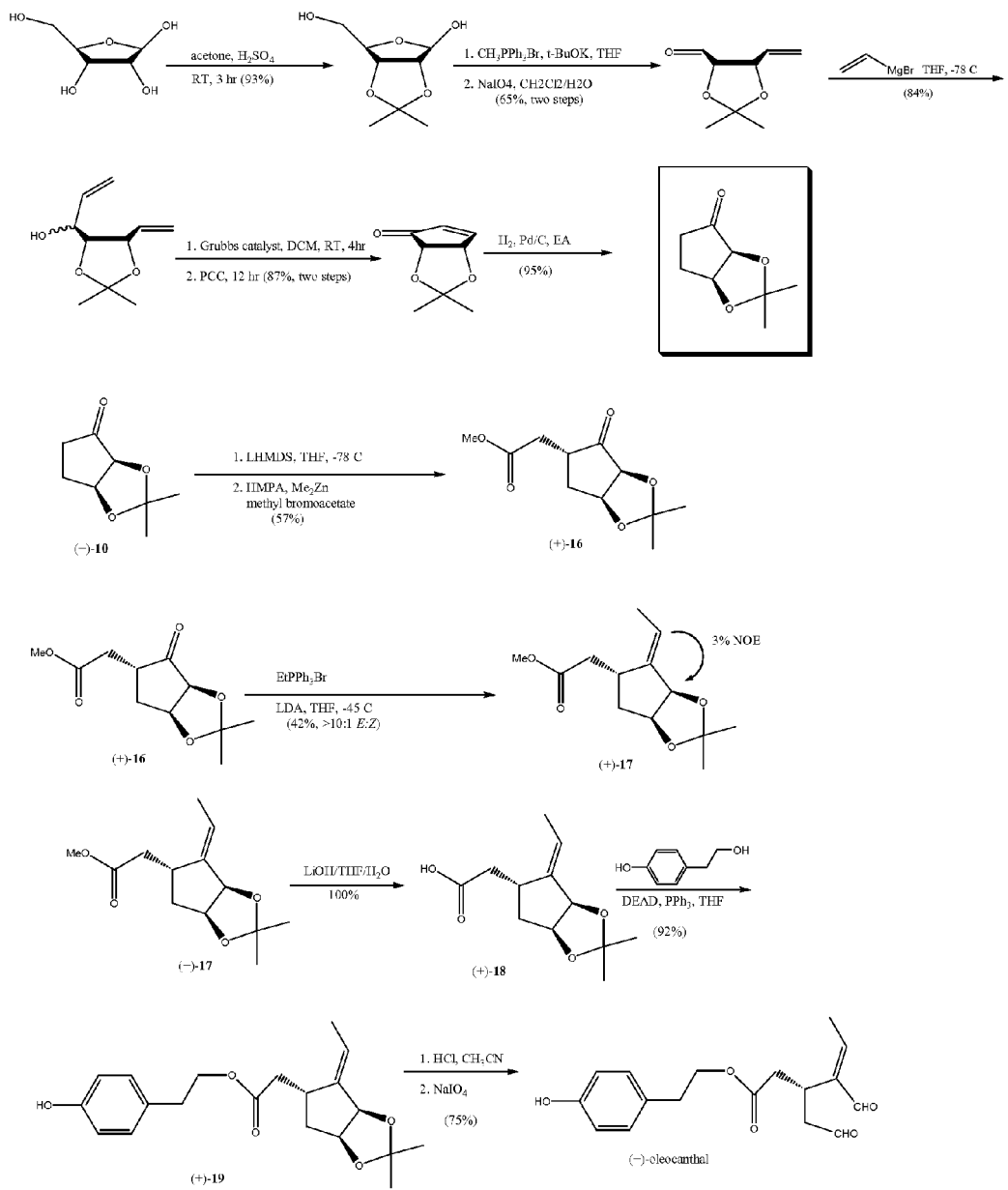
FIG. 4 shows the synthetic scheme of (+)-oleocanthal.

D-ribose may be converted to Formula XI with a strong acid (e.g., hydrochloric acid) in acetone to yield Formula XI. The compound of Formula XI may be treated with methyltriphenylphosphine bromide (or iodide) followed by oxidative cleavage of the diol to yield a compound of Formula IIb. Thereafter the compound of Formula IIb may be contacted with a $CH_2$=CH—MgBr in a suitable solvent (e.g., tetrahydrofuran) to yield a compound of Formula IIIb which is converted to a compound of Formula IVb by treatment with Grubbs catalyst in a suitable solvent (e.g., dichloromethane (DCM)) followed by treatment with an oxidizing reagent (e.g., pyridinium chlorochromate) (PCC) or $MnO_2$). The compound of Formula IVb is contacted with hydrogen, catalyst in a suitable solvent (e.g., ethyl acetate (EtOAc)) to yield (+)-cyclopentanone (Formula Vb). The (+)-cyclopentanone (Formula Vb) is treated with lithium hexamethyldisilazide (LHMDS) followed by hexamethyl phosphoramide (HMPA), dimethyl zinc and alkyl bromoacetate (eg., methyl, ethyl, tert-butyl) to yield (+)-(3,4-dimethoxy-2-oxo-cyclopentyl)-acetic acid ester (Formula VIb). The compound of Formula VIb is subjected to a Wittig ethylnation using ethyltriphenylphosphine bromide (or iodide) at reduced temperature, preferably −40° C. or less. The ester is hydrolyzed (Formula VIIIb) and the compound of formula VIIIb is contacted with 4-hydroxyphenethyl alcohol in the presence of phosphine, dialkyl azodicarboxylate (e.g., diethyl or diisopropyl) (DEAD or DIAD) to give the Formula IXb. The vicinal diol moiety is liberated and oxidative cleavage yields the (+)-oleocanthal (Formula Xb). See also FIG. 4.

The invention contemplates mimetics of oleocanthal that have the general formula I or XII shown above. Mimetics or mimics of oleocanthal (sterically similar compounds formulated to mimic the key portions of the structure) may be designed for pharmaceutical use. Mimetics may be used in the same manner as oleocanthal, and hence are functional equivalents. The generation of a structural-functional equivalent may be achieved by the techniques of modeling and chemical design known to those of skill in the art. It will be understood that all such sterically similar constructs fall within the scope of the present invention.

The design of mimetics to a known pharmaceutically active compound is a known approach to the development of pharmaceuticals based on a "lead" compound. This is desirable where, for example, the active compound is difficult or expensive to synthesize, or where it is unsuitable for a particular method of administration, e.g., some peptides may be unsuitable active agents for oral compositions as they tend to be quickly degraded by proteases in the alimentary canal.

There are several steps commonly taken in the design of a mimetic. First, the particular parts of the compound that are critical and/or important in determining its organoleptic properties are determined. In the case of oleocanthal, this can be done, for example, by systematically varying the R groups of the general formula and testing for anti-inflammatory activity, such as, for example, by the assays described in the Examples.

Once the active region of the compound has been identified, its structure is modeled according to its physical properties, e.g., stereochemistry, bonding, size, and/or charge, using data from a range of sources, such as, but not limited to, spectroscopic techniques, X-ray diffraction data, and NMR. Computational analysis, similarity mapping (which models the charge and/or volume of the active region, rather than the bonding between atoms), and other techniques known to those of skill in the art can be used in this modeling process. In a variant of this approach, the three-dimensional structure of the compound is modeled.

A candidate general formula is selected onto which chemical groups that mimic oleocanthal can be grafted. The general formula and the chemical groups grafted onto it can conveniently be selected so that the mimetic is easy to synthesize, is pharmacologically acceptable, and does not degrade in vivo, while retaining the biological activity of oleocanthal. Further optimization or modification can then be performed to arrive at one or more final mimetics for in vivo or clinical testing.

Uses of Oleocanthals

A. As a Food Additive:

The oleocanthals of the invention provide the characteristic irritation sensation found in premium olive oils. The oleocanthals may be added to lower grade oils to provide for an oil that tastes like premium extra virgin olive oil. As such, the oleocanthals act as a flavorant or flavor enhancer. The oleocanthals and formulations of the invention may also be added to other foods to enhance the flavor or the food by providing a pleasing irritation sensation of olive oil.

The oleocanthals of the invention may be added to foods and oral pharmaceutical preparations and oral hygiene products such as toothpaste, mouthwash, breath-fresheners, films, candies, lozenges to provide an irritant for the oral product's sensory-irritation experience.

Oleocanthals may also provide sweetness inhibition, or allow the structural design of other sweetness inhibitors. Such sweetness inhibitors are useful when carbohydrates are added for bulking and altering food body and texture.

Finally, oleocanthals may be used to add an irritant to food for enhancing the flavor and gastronomic experience in a similar fashion to other spices such as chilis, mustards, onions, Szechwan pepper, and ginger, for example.

B. Preservative:

The oleocanthals and formulations of the invention may be added directly to food items to act as a preservative. The food items may be for human consumption or animal consumption. Especially preferred food items for the method of preservation are items which are customarily stored in oil. In this method a suitable and effective amount of one or more oleocanthals or a formulation thereof is added directly to the food item or oil in which the food item is stored.

In another embodiment of the invention, the oleocanthals or formulation thereof is used to coat the food item prior to packaging. The formulation may be sprayed onto the food item or the food item may be dipped in the formulation. In another embodiment, the oleocanthals or formulation thereof is applied to the inside surface of packaging material that is in contact with the food item to prevent spoilage. The coating may be a thin film sprayed onto the inner surface or laminated onto the inner surface, for example. In another embodiment of the invention, the packaging material used to store the food item is impregnated with one or more oleocanthals or a formulation thereof. All of the embodiments for incorporating a preservative into packaging materials or for incorporating a preservative in food are well-known in the art, and any suitable means may be employed. Without wishing to be bound by any particular theory of operation, the preservative formulations and oleocanthals possess anti-bacterial and antifungal properties which allow them to act as preservatives.

C. Pharmaceutical Formulations

When employed as pharmaceuticals, the oleocanthals of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain other active ingredients in addition to the one or more oleocanthals with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, 1-10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 1 g, more usually about 1 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I or XII above is employed at about 20 weight percent of the pharmaceutical composition or less, more preferably about 15 weight percent or less, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Of course, additionally, the compositions of the present invention may be formulated in sustained release form to provide the rate controlled release of any one or more of the components to optimize the therapeutic effects while minimizing undesirable side effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, olive oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable carrier materials. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

(1) Cold Symptom Relief:

The oleocanthals of the invention may be used in a method for treating the symptoms of the cold or flu. Formulations may be prepared containing oleocanthals as the active ingredient, or in combination with other active ingredients to be taken orally, rectally, intranasally or as an inhalant, for example.

When taken orally, the formulation comprising one or more oleocanthals may be in the form of a lollipop, quick-dissolving film, tablet, syrup, liquid, liqui-gel, capsule, or the like.

The amount of oleocanthals in the preparation may be adjusted by a physician of skill in the art for suitable dosages for adults or pediatric use, or by a veterinarian of skill in the art for use in various animals. The dosage of drug may be determined based on the weight of the subject or based on surface area. Any method of determining proper dosages is acceptable.

The oleocanthals are preferably formulated with a pharmaceutically acceptable diluent, excipient or carrier (collectively referred to herein as "carrier" materials) as described above.

(2) Counter-Irritant for Sore Throat:

The oleocanthals of the invention are useful as counter-irritants for sore throat which may accompany a cold or flu, for example. One or more oleocanthals may be applied in combination with other ingredients for sore throat relief or may be provided as the sole active ingredient. The oleocanthal-based sore throat formulations may be in the form of a tablet, lozenge, lollipop, chewing gum, or throat spray. The formulation may be prepared and packaged by any means known in the art.

For example, solid dosage forms may contain other ingredients known in such dosage forms such as acidity regulators, opacifiers, stabilizing agents, buffering agents, flavorings, sweeteners, coloring agents, and preservatives. For example, a lozenge may be prepared as by heating the lozenge base (e.g., a mixture of sugar and liquid glucose) under a vacuum to remove excess water and the remaining components are then blended into the mixture. The resulting mixture is then drawn into desired shape. The lozenges are cooled, and packaged into suitable packaging. Lozenges will normally be sucked by the patient to release the oleocanthal or oleocanthal analog. Chewable solid dose formulations may be made by the methods used to prepare chewable candy products or chewing gums. For example, a chewable solid dosage form may be prepared from an extruded mixture of sugar and glucose syrup to which the one or more oleocanthals has been added with optional addition of whipping agents, humectants, lubricants, flavors and colorings. (See Pharmaceutical Dosage Forms: Tablets, Volume 1, Second Edition edited by H A Lieberman, L Lachman and J B Schwartz published in 1989).

Spray formulations may be prepared by dissolving or suspending the one or more oleocanthals in a liquid medium which may also contain other ingredients such as stabilizing agents, buffering agents, flavorings, sweeteners, coloring agents, and preservatives. For example, a spray may be prepared by dissolving water soluble components in water and non-water soluble ingredients in a co-solvent (e.g., alcohol). The two phases are then mixed and the resulting mixture filtered and placed into dispensing containers. The dispensing containers may be fitted with a metered, manually-operated spray mechanism or the dispenser may contain a pressurized propellant and be fitted with a suitable dispensing valve.

(3) Nasal Decongestant:

The oleocanthals of the invention are useful as a nasal decongestant. The one or more oleocanthals may be applied in combination with other nasal decongestants or may be provided as the sole active ingredient. The oleocanthal-based nasal formulations may be in the form of a lavage or nasal mist. The formulation may be prepared and packaged by any means known in the art for nasal lavages and mists.

(4) Antioxidant:

Oleocanthals are believed to have anti-oxidant activity and as such may be used to treat or prevent various conditions including cancer. The oleocanthals may also be used to promote wound healing, either by application directly onto wounds, or as a coating or impregnation of bandages, sutures and the like.

The antioxidant effects of oleocanthals may also be exploited in the formulation of cosmetics. The compositions can protective of skin or hair or as an anti-solar composition. In accordance with the invention the compound of formula (I) or (XII), and preferably one or more oleocanthals is generally present in an amount ranging from 1 to 1,000 mg. In some embodiments, one or more oleocanthals are present in an amount of about 5 to 800 mg. In other embodiments, one or more oleocanthals are present in an amount of about 10 to 750 mg. In other embodiments, one or more oleocanthals are present in an amount of about 25 to 600 mg. In other embodiments, one or more oleocanthals are present in an amount of about 50 to 500 mg. In certain embodiments, one or more oleocanthals are present in 1, 5, 10, 20, 25, 50, 75, 100, 125, 200, 250, 300, 350, 400, 450, 500, 550, 600, 650, 700, 750, 800, 850, 900, 950 or 1,000 mg.

In the compositions according to the present invention, the compound of formula (I) or XII acts as an antioxidant agent. These compositions can be capillary compositions such as hair lacquers, hair setting lotions or hair treating or disentangling lotions, shampoos, coloring shampoos, hair dye compositions, makeup products such as nail enamels, skin treating creams and oils, foundations, lipsticks, compositions for the care of the skin such as bath oils or creams as well as any other cosmetic composition capable of exhibiting, because of their components, oxidation stability problems during storage.

(5) Pain Relief:

The oleocanthals of the invention may be used as to treat and prevent pain. The compounds are useful for the relief of pain associated with a variety of conditions including, but not limited to influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, cancer and for pain associated with surgical and dental procedures.

(6) Anti-Inflammatory:

The oleocanthals of the invention may be used as anti-inflammatory agents. The oleocanthals may be used in a method for treating or preventing diseases marked by inflammation, including but not limited to psoriasis, cancer, asthma, allergic rhinitis, respiratory distress syndrome, inflammatory bowel disease, Crohn's disease, gastritis, irritable bowel syndrome, ulcerative colitis, migraine, periarteritis nodosa, thyroiditis, aplastic anemia, Hodgkin's disease, scleroderma, type I diabetes, myasthenia gravis, multiple sclerosis, sorcoidosis, ischemic kidney disease, nephrotic syndrome, Bechet's syndrome, polymyositis, gingivitis, conjunctivitis, vascular disease myocardial ischemia, heart disease, stroke, and hypertension.

(7) Micro-G Protein and Associated Kinase Inhibitor:

The oleocanthals of the invention may also be formulated for treatment or prevention of the development of Aβ42 associated Alzheimer's plaques and tangles in a manner similar to that found for non-steroidal anti-inflammatory drugs such as ibuprofen. Without wishing to be bound by any particular theory of operation, it is believed that ibuprofen and oleocanthal inhibit micro-G proteins and associated kinases, for example Ras and Rock, which have been associated with the development of Aβ42 associated plaques and tangles in the brains of Alzheimer's patients. Oleocanthals also acts to inhibit γ-secretases and alter presenilin conformations of which both activities are associated with reducing Aβ42 associated Alzheimer's plaques and tangles.

It is believed that certain non-steroidal anti-inflammatory drugs inhibit γ-secretases without significantly altering other activities in the Aβ amyloid precursor protein (APP) processing pathway. In patients with certain mutations in APP and all mutations known for presenilin, APP is processed such that there is a large increase in the amount of a proteolytic fragment of 40-42 residues (Aβ42) (Weggen et al. (2001) Nature 414(8):212). Certain NSAIDs appear to have an effect of reducing the production of Aβ42 by a mechanism that is independent of the cyclooxygenase activity associated with the anti-inflammatory activity of the NSAIDs. It has been shown that for many NSAIDs, which are administered as racemic mixtures of the active compounds, that a specific enantiomer (the S-enantiomer) appears to be responsible for the inhibition of cyclooxygenase activity, and hence the anti-inflammatory effect (Weggen et al. (2001) Nature 414(8): 212). It has also been shown that the R-enantiomer of the NSAIDs may mediate reduction of Aβ42 production and may be responsible for the decreased risk in Alzheimer's and cognitive impairment seen with long term use of NSAIDs (Morihara et al. (2002) J. Neurochem. 83:1009-1012).

Also correlating with lower risk of developing Alzheimer's and cognitive impairment is the so-called Mediterranean diet, which is typically high in consumption of, among other things, olive oil. Thus, the observation made herein of the association with the organoleptic properties of oleocanthal and the similarity to ibuprofen and the observations associated with long term use of NSAIDs and dietary intake of olive oil suggest that oleocanthal may be used for the treatment and prevention of neurodegenerative disorders (e.g., Alzheimer's and other cognitive impairment associated with amyloid plaques and tangles). The treatment and prevention of such neurodegenerative disorders may be performed using a racemic mixture of oleocanthal, or may be using one of the purified enantiomers of oleocanthal.

(8) For Oral Surgery and Oral Irradiation Treatment of Cancer:

The oleocanthals of the present invention are also useful as treatments for use in conjunction with oral surgery and oral irradiation treatment of cancer. While not wishing to be bound by any particular theory of operation, it is believed that the oleocanthals, with their attendant anti-inflammatory activity, act to inhibit the inflammation that occurs in the oral cavity as a result of surgery or oral irradiation. The oleocanthals may be formed as an oral rinse which can be administered before the procedure, after the procedure, or during the procedure, or a combination of these treatment regimens. The amount of oleocanthal or oleocanthal analog in the rinse is a therapeutically effective amount which is readily determined by one of skill in the art.

D. Animal Repellant:

It is believed that oleocanthals, with their organoleptic qualities, are useful as animal repellents. The compounds may be used to repel carnivorous and omnivorous animals and birds, including domestic cats, rodents, raccoons, dogs, other canids such as coyotes.

The method of this invention comprises applying an effective, repellent amount of the oleocanthals, either alone or in combination with a suitable carrier, to the locus from which the animals are to be repelled. Suitable carriers would include liquid diluents such as water, hydrocarbons, alcohols, emulsifiers and other liquids generally found in household spray formulations or pharmaceutical preparations so as to be acceptable from a human safety viewpoint. Inert solid carriers such as starches may also be of use, and it might be desirable to incorporate the compounds into a controlled-release formulation.

It may be desirable to apply the oleocanthals to containers for discarded edible refuse, such as metal or plastic garbage cans, plastic bags, paper and cardboard boxes and the like.

Further, the repellent compounds disclosed herein might be incorporated into various potentially-edible compositions which, if consumed, could injure or kill an animal. An example of such a composition would be liquid antifreeze.

Another aspect of this invention provides methods for repelling birds from consuming or utilizing a material otherwise susceptible to consumption or utilization by birds, comprising providing to the material an avian repellent amount of at least one oleocanthal or oleocanthal analog.

Liquid carriers may be employed and the repellent may be sprayed on the material. See e.g., U.S. Pat. No. 2,967,128 which patent is incorporated by reference as if fully set forth herein. The compound may be dispersed in the liquid from which the birds are to be repelled. The repellent may be at least partially trapped in a solid vehicle to improve its persistency such as disclosed in U.S. Pat. No. 4,790,990. The vehicle may be a modified starch, oil or polymer which at least partially encapsulates, emulsifies or substantially uniformly disperses the aversive agent. The repellent compound and vehicle may be dispersed throughout solids consumed by avian species to reduce the likelihood that they will eat the treated edible.

Certain embodiments of the present invention are directed to methods of repelling birds from consuming or utilizing non-potable liquids such as industrial or agricultural waste water, mine tailing ponds, and freestanding water on artificial surfaces like airport runways and parking lots. "Non-potable" refers to liquids or aquatic habitats wherein said liquid may be consumed or utilized by birds to the detriment of man or the birds.

E. Discovery

Knowledge of the absolute structure of oleocanthal allows the identification of the oleocanthal receptor and related genes. Screening assays for receptors, well-known in the art, may be employed to determine the oleocanthal receptor. Tissue from the back of the throat, known to interact with oleocanthal may be isolated and subjected to various assays to determine the binding of oleocanthal to cells and the molecular signaling pathway of oleocanthals.

Labeled oleocanthal or oleocanthal analog may be used in tissue binding studies to determine the cell types that contain a presumptive oleocanthal receptor. Cells that have bound labeled oleocanthal or analog may be visualized by any method known in the art. For example, but not by way of limitation, oleocanthal or an analog may be labeled with a radiolabel (e.g., $^{125}$I, $^{35}$S, $^{32}$P, $^{33}$P, $^{3}$H), a fluorescence label, a chemiluminescent label, an enzymatic label, or an immunogenic label. In other embodiments, luminescent or fluorescent molecules may be conjugated to the oleocanthal molecule. The labeled oleocanthal or analog may be allowed to bind to cells in situ and visualized under a microscope. Alternatively, cells in suspension may be labeled with the labeled oleocanthal or oleocanthal analog and labeled cells may be separated from unlabeled cells by flow cytometry or using a sorter, such as a fluorescence-activated cell sorter (FACS). Labeled cells may be collected for subsequent genetic analysis, for example.

In some embodiments, a molecule is conjugated to oleocanthal or an oleocanthal analog that allows the conjugated oleocanthal or oleocanthal analog to be cross-linked to its receptor upon binding. This may be performed by any means known in the art. Thereafter the cross-linked receptor may be isolated from the cells, purified and subjected to N-terminal amino acid sequencing. With the identity of the N-terminal amino acids, degenerate oligonucleotides may be synthesized based on the possible combinations of oligonucleotides encoding the amino acid sequence and the oligonucleotides may be used in various ways to identify the gene encoding the oleocanthal receptor. In some embodiments, the degenerate oligonucleotides are used to probe gene libraries. The gene library may a library formed from animal cells, particularly human cells, or it may be a specific cell-type library from animal cells known to be responsive to oleocanthal. In other embodiments, the library may be a subtractive library formed by removing commonly expressed genes from oleocanthal-responsive and oleocanthal-unresponsive cells, such that the library consists of a subset of genes reflecting unique sequences of the oleocanthal-responsive cells. In another embodiment, the degenerate oligonucleotides are paired with a second set of oligonucleotides to allow rt-PCR amplification of polynucleotides containing the sequences encoding the amino acid sequence of the oleocanthal receptor. Such second set of oligonucleotides may include, for example, oligo-dT which anneals to poly-adenosine tracts of mRNA. The rt-PCT reaction may be performed on RNA extracted from oleocanthal responsive cells. The methods and techniques for such genetic analysis are well-known in the art and may be found in the references and texts referred to herein.

Further aspects of the invention are exemplified below, however, the examples are merely illustrative of the invention and the scope of the invention is not to be limited thereto or thereby.

EXAMPLES

Example 1

Isolation of deacetoxydialdehydic ligstroside aglycone "Oleocanthal"

A. Synthesis of Oleocanthal

Retrosynthetically, we envisioned both enantiomers of (1) to derive from the enantiomeric forms of cyclopentanediols (7) via oxidative cleavage of the diol moiety (Scheme 1). The requisite cyclopentanediols (7) in turn would be prepared from cyclopentanones (+)- and (−)-(10), via alkylation to introduce stereoselectively the side chain from the convex face, followed by stereoselective Wittig ethylnation and removal of the acetonide moiety (Scheme 1).

SCHEME 1

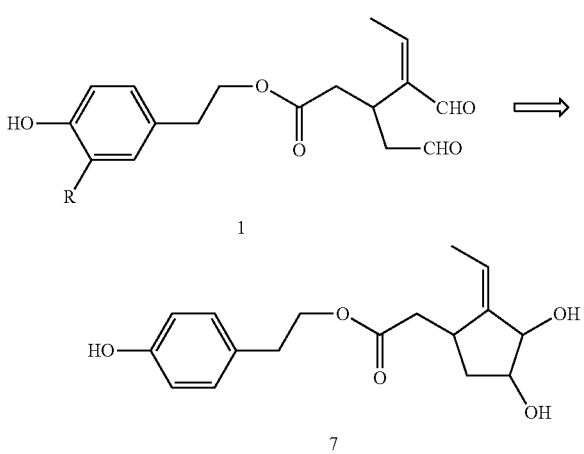

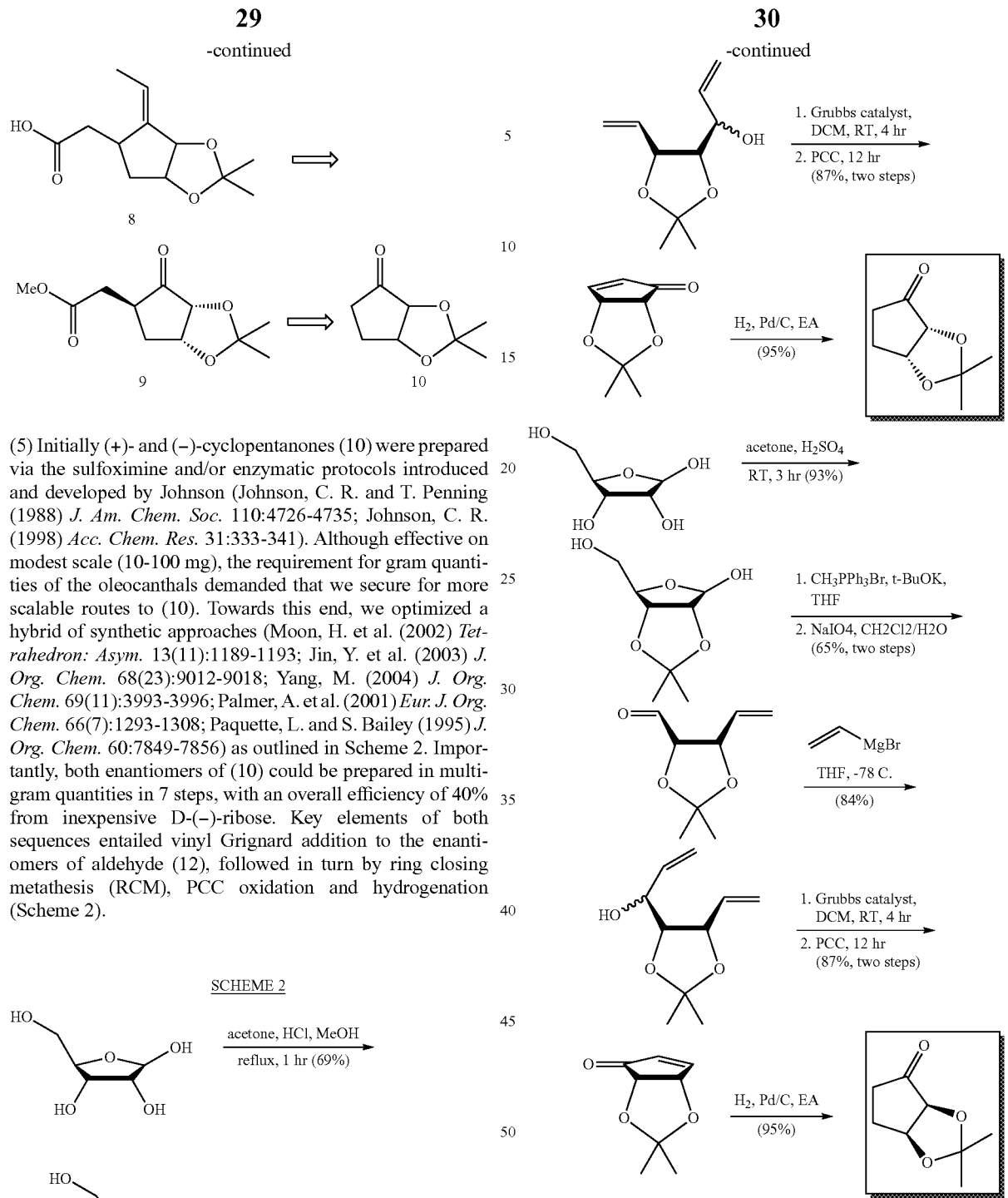

(5) Initially (+)- and (−)-cyclopentanones (10) were prepared via the sulfoximine and/or enzymatic protocols introduced and developed by Johnson (Johnson, C. R. and T. Penning (1988) *J. Am. Chem. Soc.* 110:4726-4735; Johnson, C. R. (1998) *Acc. Chem. Res.* 31:333-341). Although effective on modest scale (10-100 mg), the requirement for gram quantities of the oleocanthals demanded that we secure for more scalable routes to (10). Towards this end, we optimized a hybrid of synthetic approaches (Moon, H. et al. (2002) *Tetrahedron: Asym.* 13(11):1189-1193; Jin, Y. et al. (2003) *J. Org. Chem.* 68(23):9012-9018; Yang, M. (2004) *J. Org. Chem.* 69(11):3993-3996; Palmer, A. et al. (2001) *Eur. J. Org. Chem.* 66(7):1293-1308; Paquette, L. and S. Bailey (1995) *J. Org. Chem.* 60:7849-7856) as outlined in Scheme 2. Importantly, both enantiomers of (10) could be prepared in multigram quantities in 7 steps, with an overall efficiency of 40% from inexpensive D-(−)-ribose. Key elements of both sequences entailed vinyl Grignard addition to the enantiomers of aldehyde (12), followed in turn by ring closing metathesis (RCM), PCC oxidation and hydrogenation (Scheme 2).

Alkylation of (+)- and (−)-cyclopentanone (10) with methyl bromoacetate was then anticipated to proceed from the less hindered convex face of the bicyclic skeleton to install the side chain in a stereoselective fashion. Initial attempts however to alkylate (−)-(8) with methyl bromoacetate employing LDA in the presence of HMPA furnished only a complex mixture containing only trace amounts of (−)-(16). Neither addition of Cu(I) (Johnson, C. R. and T. Penning (1988) *J. Am. Chem. Soc.* 110:4726-4735) reportedly to suppress side reactions, nor the use of the corresponding tin enolate [generated by treatment of (−)-(10) in THF with LDA, followed by HMPA and tributyltin chloride (Suzuki, M. et al. (1985) *J. Am. Chem. Soc.* 107:3348; Nishiyama, H. et al.

(1984) *Tetrahedron Lett.* 25:223)] improved the situation. Alkylation of the zinc enolate of (−)-(10) [generated by treatment of (−)-(10) in THF with 1.1 eq. LHMDS, followed in turn by HMPA (3.0 eq.) and dimethyl zinc (Morita, Y. et al. (1989) *J. Org. Chem.* 54:1787-1788) (1.0 eq.)] with methyl bromoacetate, however consistently furnished (−)-(16) in 55-60% yield as a single diastereomer (this reaction was fairly clean except some baseline materials. Using t-butyl bromoacetate instead of methyl bromoacetate did not improve the yield) (Scheme 3).

SCHEME 3

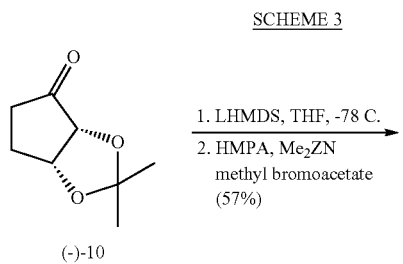

(−)-10

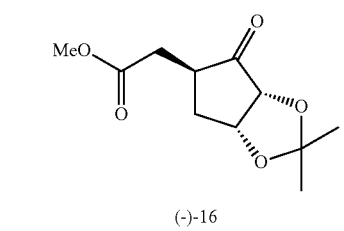

(−)-16

Wittig ethylnation of (−)-(16) was next achieved with ethyltriphenylphosphine bromide. Best results were obtained employing LDA as the base at −45° C. Although excellent stereoselectivity (ca., 10:1 E:Z) favoring the E-isomer (−)-(17) was achieved, the yield was only modest (42%), presumably due to the ease of enolization of (−)-(16) (Edmunds, M. "The Wittig Reaction" In MODERN CARBONYL OLEFINATION, Takeda, Ed., John Wiley & Sons, New Jersey, 2004). Interestingly, the stereoselectivity varied dramatically with reaction temperature. At 0° C., the E:Z selectivity was 3.3:1, while at room temperature the selectivity was 1.6:1. Assignment of the E geometry of the olefin was based on NMR NOE analysis (Scheme 4).

SCHEME 4

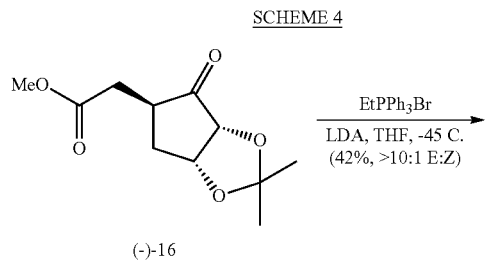

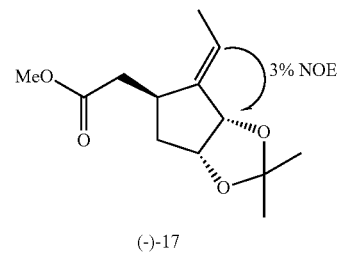

(−)-17

Hydrolysis of ester (−)-(17) (LiOH/THF/H$_2$O) next afforded acid (−)-(18), which was subjected to Mitsunobu esterification (Mitsunobu, O. (1981) *Synthesis* 1-28) with 4-hydroxyphenethyl alcohol to furnish phenol (−)-(19) in 92% yield. As expected, the Mitsunobu reaction proceeded with complete chemoselectivety at the primary hydroxyl (Appendino, G. et al. (2002) *Org. Lett.* 4:3839-3841). Completion of the synthesis of (−)-oleocanthal (1) was then achieved via liberation of the vicinal diol moiety (4N HCl/acetonitrile), followed by oxidative cleavage (NaIO$_4$); (−)-oleocanthal (1) was identical in all respects (e.g., $^1$H and $^{13}$C NMR, IR and HRMS) with an authentic sample isolated from virgin olive oil, the latter possessing spectral data identical to that reported in the literature (Montedoro, G. et al. (1993) *J. Agric. Food Chem.* 41:2228-2234). The structural assignment of (1) was also confirmed by COSY NMR analysis. Synthetic (−)-(1) displayed a small negative optical rotation ($[\alpha]^{25}_D$ −0.78, c=0.9, CHCl$_3$) identical to that obtained from a sample isolated from virgin olive oil ($[\alpha]^{25}_D$ −0.9, c=2.0, CHCl$_3$). Thus the stereochemistry of (−)-oleocanthal (1) is 3S, 4E. The enantiomer of the natural product (+)-(1) was prepared via a similar reaction sequence beginning with (+)-(10) to furnish (+)-1 ($[a]^{25}_D$ +0.73, c=0.55, CHCl$_3$) (Scheme 5).

SCHEME 5

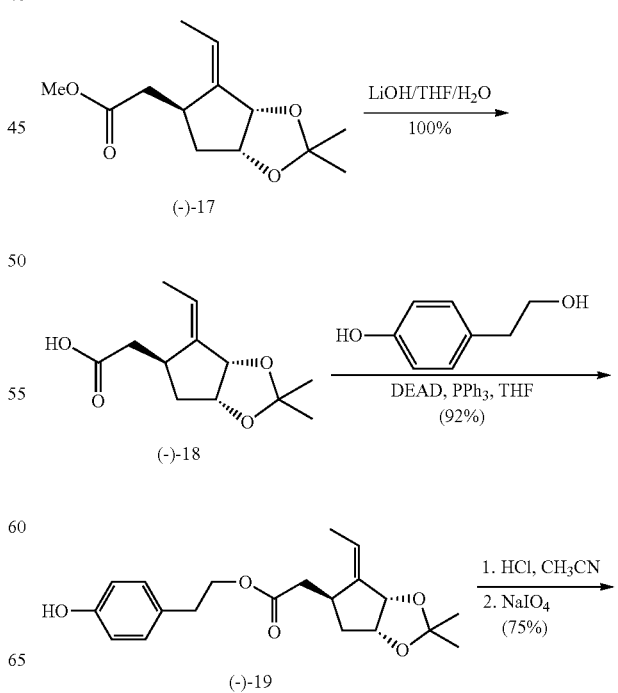

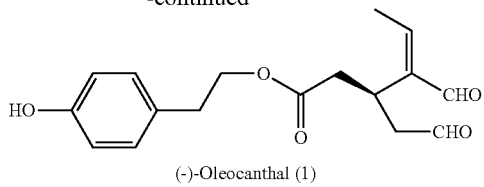

(-)-Oleocanthal (1)

In summary, an effective, scalable synthesis of both enantiomers of oleocanthal (1) has been achieved, each in 13 steps (7% overall yield) from inexpensive (D)-(−)-ribose, requiring only 6 chromatographic separations. The structural similarity of oleocanthal to a number of related natural products (Somanadhan, B. et al. (1998) *Planta Medica* 64:246-50; Takenaka, Y. et al. (2002) *Chem. & Pharm. Bull.* 50(3):384-389; Takenaka, Y. et al. (2002) *Phytochemistry* 59(7):779-787) suggests that the synthetic approach presented here should also be applicable to their construction.

B. Functional Studies of Oleocanthal

This restricted throat irritation of oleocanthal is remarkably similar to that elicited by ibuprofen. Due to the observed organoleptic similarity, we isolated and then synthesized oleocanthal from olive oil. Sensory and chemical evaluation of 10 commercially available olive oils revealed a strong positive relationship between throat irritation intensity and oleocanthal concentration. Cyclooxygenase and lipoxygenase assays with synthesized oleocanthal demonstrated that it is a NSAID with an anti-inflammatory profile strikingly similar to that of ibuprofen, in accordance with its sensory properties. Oleocanthal may play a significant role in the well-known health benefits associated with a diet high in olive oil. Moreover, identification of other pharmacologically important compounds is hereby facilitated by attention to similarities of sensory properties.

Recent studies in our laboratories have demonstrated that ibuprofen, as well as some other non-steroidal anti-inflammatory drugs (NSAIDs), have the unusual sensory property of stinging almost exclusively in the throat, unlike for example, capsaicin and piperine that also burn the mouth and lips. While tasting newly-pressed Sicilian olive oil, it was observed that the throat-irritating sensation appeared identical to that of ibuprofen. Indeed, high quality extra virgin olive oils are often characterized by a stinging or burning sensation akin to that felt when swallowing ibuprofen. With olive oil, this sensation often elicits a small cough or throat-clearing when olive oil is swallowed neat. Olive oil enthusiast categorize oils as 0, 1, 2 or 3 cough oils with the higher numbers being superior. The entity responsible for this sensory property has recently been reported to be deacetoxy-dialdehydic ligstroside aglycone, one of many polyphenols found in olive oil.

Based on their similar oro-sensory properties, we reasoned that oleocanthal might also share pharmacologic properties of ibuprofen. To test this thesis, we first had to verify and definitely prove the identity of oleocanthal. This required development of an efficient analytical method for isolating and quantifying it. Two approaches to verify the identity of the compound and its properties were taken. First, we undertook psychophysical experiments with oleocanthal, correlating the amount of identified compound with the degree of burn in commercial olive oils. Second, we synthesized oleocanthal and tested the psychophysical properties of the synthesized material. Finally, to examine oleocanthal for pharmacological activity that might mimic ibuprofen, cyclooxygenase, lipoxygenase and lipid peroxidation assays with synthetic material were conducted.

To isolate and purify oleocanthal, we employed a systematic sensory-directed approach. That is, we used taste analysis as a tool to monitor the presence of the throat-irritation compound in each step of an isolation and purification procedure similar to that used by Andrewes et al. Briefly, the irritant was first extracted from olive oil with methanol/water (80/20, v/v). The phenolic extract was separated into 15 fractions, only one of which was irritating, using a reversed-phase HPLC method. To obtain pure material, we pre-fractioned the olive oil phenolic extract on a C18 solid phase extraction cartridge. Retention information about the throat-irritating principal from the HPLC method allowed us to separate it from the majority of the other co-extracted phenolic compounds using methanol and water solvent mixtures at three different ratios of eluting solvents. HPLC analysis of the throat irritating fraction revealed the presence of several unresolved compounds. A new HPLC gradient was thus developed and only one well-resolved peak was throat-irritating. A detailed NMR (1D and 2D) analysis was conducted with this material. Although $^1$H-NMR spectra indicated the presence of minor impurities, the structure of the major compounds was readily identified to be 2-(4-hydroxyphenyl)ethyl, 4-formyl-3-(2-oxoethyl)-4-hexenoic acid ester, the deacetoxy-dialdehydic ligstroside aglycone, as first identified in olive oil by Montedoro and recently reported as the throat irritant. Optical rotation measurements of oleocanthal revealed the natural enantiomer to be levorotary.

Olive oils differ markedly in their ability to elicit throat irritation. If oleocanthal is primarily responsible for this sensory property there should be a positive relation between compound concentration and degree of throat irritation. To test this hypothesis, we purchased 10 different olive oils with widely varying degrees of throat irritation based on informal evaluation. The amount of oleocanthal in each was then quantified. The compound was extracted from small amounts of each of the 10 oils (1 g) by hexane-acetonitrile (liquid-liquid) extraction. The solvent extract was analyzed by reverse-phase HPLC with UV detection at 278 nm. Oleocanthal was chromatographically separated from the other extracted compounds with an elution gradient of acetonitrile and water. All analyses were done in duplicate using solutions of pure, isolated oleocanthal as the external standard. When the compound was later synthesized, this was also used as a standard to confirm these methods. Overall, the reproducibility was high (RSD=4.7%), recovery was good (95%), the calibration curve was linear ($r^2$=0.9999) and the limit of quantitation was <1 ppm.

The degree of throat irritation of these 10 oils was quantified by 17 volunteers. Each subject was tested only 2 times per day with two different olive oils samples with 1-2 hours separating each test since the irritation may be sensitive to shorter inter-trial intervals. Subjects wore nose clips to eliminate olfactory cues. Tasting consisted of placing approximately 3.5 ml of olive oil in the mouth, holding it there for 3 seconds and then swallowing it in two aliquots so as to insure the throat would be stimulated. After 45 seconds passed, subjects were asked to rate the peak throat irritation sensitivity using the general labeled magnitude scale, a sensory scale developed to generate magnitude estimation-like quality data. Each subject was tested twice with all ten oils.

Figure 2:
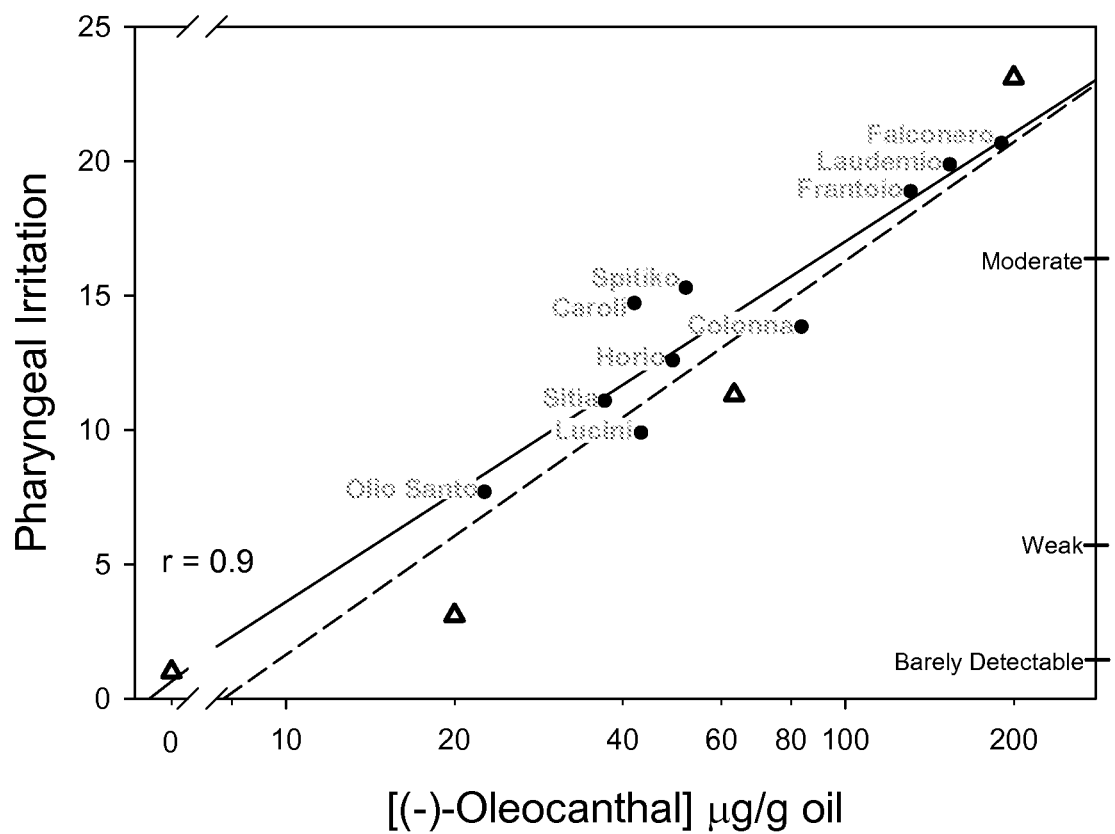
FIG. 2 shows a graph of the irritation intensity of various olive oils plotted against their concentrations of oleocanthal.

The concentrations of oleocanthal in the 10 olive oils and their degree of throat irritation proved statistically significant (r=0.90; FIG. 2) providing additional evidence that oleocanthal is responsible for the majority of the throat irritation in the olive oils tested.

These studies strongly implicate oleocanthal as the major throat irritating compound in olive oil. Nevertheless, as noted by Andrewes et al., co-elution of a minor component or mixture of components causing the burning sensation cannot be eliminated as a possible source of irritation without completing a de novo total synthesis followed by organoleptic analysis. Since the structure of oleocanthal possesses a stereospecific center, we synthesized both enantiomers from readily available D-ribose. The synthesis of both (+) and (−)-oleocanthal required 13 steps as outlined for the recovery of levorotary (−)-enantiomer in FIGS. 3 and 4. Both syntheses proved scalable, proceeding in 7% overall yield and thereby providing ample material for sensory and pharmacological evaluation. The levoratory (−)-enantiomer of synthetic oleocanthal displayed the same sign and magnitude of the optical rotation as the natural material. Thus the absolute stereodirection of variant (1) is as depicted in FIG. 2.

Three individuals experienced in tasting olive oils and ibuprofen, using a standard 2 alternative forced-choice method, evaluated the synthetic compound (the natural (−)-isomer only) dispersed in non-irritating corn oil at approximately twice the concentration found in Falconaro olive oil, the most potent olive oil we have evaluated (FIG. 1).

Testing was double-blind and each was exposed to three sets of two samples, one of which was added synthesized oleocanthal and the other served as the blank control. The task was to indicated which of the pair was more irritating. Each of the three evaluators correctly identified the sample on each of the three presentations (9 of 9 correct, p<0.01) and all three identified the distinct back of the throat irritation with the cough-eliciting sensation characteristic of both olive oil and ibuprofen. As predicted, the throat irritation of synthetic (−)-oleocanthal was identical to oleocanthal isolated from premium olive oil. Importantly, the effect was dose dependent (FIG. 2 open triangles, dashed line). Ten subjects were tested with non-irritating commercial corn oils presented neat and mixed with either synthesized (−)-oleocanthal or the bitter agent sucrose octaacetate (SOA) (Sigma-Aldrich). The addition of SOA enabled forced-choice trials to be conducted without revealing to subjects the identity of the irritating samples due to bitterness or other non-irritating cues. (−)-Oleocanthal was tested at the highest concentration identified in the ten rated oils, 200 μg/ml, and at one half and whole log steps more dilute 63.25 and 20 μg/ml. SOA was added to the corn oil ($4 \times 10^{-4}$, $1 \times 10^{-4}$, $5 \times 10^{-5}$ M) to intensity match the irritation of the three levels of (−)-oleocanthal. Subjects participated in two-alternative forced-choice (2AFC) trials (four trials at every concentration for each subject) and in intensity ratings sessions (four ratings per each oil). For the 2AFC trials subjects were presented with two 3.0 ml corn oil samples with matching intensities of SOA and (−)-oleocanthal in ascending order, and were required to sample oils as described above. While blind to stimulus position, subjects were asked two questions on each trial, "Which of the two oils was more irritating in the throat?" and "Which one was more bitter?" At the 20 μg/ml & $5 \times 10^{-5}$ M level most subjects reported on some trials that the same oil was both the more irritating and the more bitter of the two. This demonstrates that participants were willing to select the one oil as stronger on both traits within a trial. Subjects performed at chance when selecting among two unadulterated corn oils, when the correct choice was randomly assigned prior to testing. At 20 μg/ml subjects were correct 24 out of 40 trials, indicating that this concentration is near detection threshold levels in corn oil. The other two concentrations were correct 39/40 and 40/40 trials. For the intensity rating trials subjects were presented with all eight oils in ascending order, counterbalanced for stimulus order and asked to rate the throat irritation and bitterness of every oil on a general labeled magnitude scale.

Assuming the quality and locus of irritation provides a signal of pharmacological activity, then oleocanthal should mimic at least some of the pharmacological properties of ibuprofen, a potent modulator of inflammation. To test this we chose to evaluate inhibition of cyclooxygenase (COX) and lipoxygenase (LO), two enzymes central to the inflammatory process. Ibuprofen is a potent COX-1 and COX-2 inhibitor but does not inhibit lipoxygenase. The concentration dependence of oleocanthal for inhibition of ovine COX-1, human recombinant COX-2 and soybean 15-lipoxygenase activities was measured using commercially available kits (Cayman Chemicals). Indomethacin was used as a positive (inhibitory) control in the cyclooxygenase assays and nordihydroguaracetic acid (NDGA) and caffeic acid were used as positive (inhibitory) controls in the lipoxygenase assays. Both enantiomers of oleocanthal, exhibited a dose-dependent inhibition of both COX-1 and COX-2 activities, with no effect on lipoxygenase activity, much as observed with ibuprofen (Table 1). The calculated $IC_{50}$ (least squares regression analysis of inhibition vs. concentration) for oleocanthal (−) was 21.4 μm and 29.4 μm for COX-1 and COX-2, respectively. The $IC_{50}$ for oleocanthal (+) was 27.9 μm and 40.5 μm for COX-1 and COX-2, respectively. In these experiments, both enantiomers of oleocanthal were more potent at equimolar concentrations than ibuprofen in inhibiting COX-1 and COX-2. Both enantiomers of oleocanthal inhibited the peroxidation of serum lipids induced by metal ions in vitro to a similar degree as equimolar alpha-tocopherol (data not shown). Thus, oleocanthal exhibits antioxidant activity comparable to alpha-tocopherol and has an arachidonic acid inhibitory profile (cyclooxygenase inhibition without lipoxygenase inhibition) indicating that both enantiomers of oleocanthal are classic NSAIDs, with potency superior to that of ibuprofen.

Taken together, these data are consistent with our hypothesis that the throat irritating compound in olive oil is an ibuprofen-like anti-inflammatory agent. Importantly, the oleocanthal results provide an example of how sensations from the mouth may serve as an in vivo pharmacological assay. These results further suggest an additional basis for the health benefits of olive oil consumption have been attributed to a combination of the lipid profile, the antioxidant activity of many of the polyphenols present and the anti-inflammatory agents that inhibit lipoxygenase. We suggest here an additional benefit: long-term consumption of oleocanthal, with anti-inflammatory ibuprofen-like activity may enhance health and well-being. Assuming that an olive oil consumer in the high normal range ingest about 50 g of olive oil per day and that this oil contains up to 200 μg/ml of oleocanthal, the person would then consume approximately 10 mg/day. Although this dose is relatively low (~10% of the dosage of ibuprofen recommended for adult pain relief), chronic low doses of other COX inhibitors (e.g., aspirin) are known to have important health benefits, chiefly a reduction in heart attack risk and at slightly higher doses a reduction in both heart attack and stroke risk.

In addition to anti-inflammatory activity, ibuprofen has recently been shown to have a COX-independent ability to decrease the highly amyloidogenic AB42 peptide, perhaps accounting for epidemiologic evidence that Alzheimer's disease. Thus, it would be important to determine whether oleocanthal has similar activity.

The initial hypothesis that the throat irritating compound in olive oil might have pharmacological activity was based on the oro-sensory similarities of ibuprofen and olive oil. This implies a similar sensory mechanism but exactly how ibuprofen (or oleocanthal) elicits almost exclusive throat irritation remains elusive. One possible explanation is that there is a currently unknown receptor system that is responsible to both ibuprofen and olive oil. Alternatively, or additionally, both compounds could have particularly easy access to free nerve endings in the throat, but why this would occur preferentially in the throat is unknown. It is also unclear why other lipophilic irritants such as lactic acid or capsaicin would not stimulate the throat exclusively as well, if the mechanism were simply one of ready access to free nerve endings. Elucidation of the sensory mechanism may assist in determining the common pathway for the anti-inflammatory activities of these molecules, or vice versa. The sensory properties of foods, spices and flavors may provide clues to pharmacological activity and thus serve not only to provide pleasure but also to enhance health.

TABLE 1

Percent inhibition of COX-1, COX-2 and 15-LO by Oleocanthal (−), (+)

| Agent | Concentration (uM) | COX-1 | COX-2 | 15-LO |
|---|---|---|---|---|
| Oleocanthal (−) | 100 | 83.5 ± 3.5 | 70.9 ± 8.6 | 0.4 ± 0.8 |
|  | 25 | 56.1 ± 3.2 | 56.6 ± 9.5 | 0.0 ± 0.0 |
|  | 7 | 24.6 ± 7.3 | 14.5 ± 2.3 | 0.0 ± 0.0 |
| Oleocanthal (+) | 100 | 68.0 ± 15.2 | 69.6 ± 3.9 | 3.5 ± 5.5 |
|  | 25 | 54.5 ± 4.6 | 41.3 ± 15.9 | 0.7 ± 1.0 |
|  | 7 | 24.6 ± 7.5 | 6.1 ± 4.2 | 0.0 ± 0.0 |
| Ibuprofen | 25 | 17.8 ± 2.3 | 12.7 ± 3.6 | 0.2 ± 0.3 |
|  | 7 | 0.0 | 1.3 | n.d. |
| Indomethacin | 25 | 45.8 ± 4.4 | 77.6 ± 10.2 | 0.1 ± 0.9 |
|  | 7 | 33.0 ± 6.1 | 71.6 ± 7.3 | 0.5 ± 0.1 |
| NDGA | 25 | n.d. | n.d. | 63.1 ± 0.8 |
|  | 7 | n.d. | n.d. | 52.5 ± 1.1 |
| Caffeic Acid | 25 | n.d. | n.d. | 25.2 ± 2.2 |
|  | 7 | n.d. | n.d. | 19.8 ± 1.3 |

*Data are presented as mean % inhibition ± SEM for three independent experiments.
N.d. = not determined.

Example 2

Structure Activity Relationship (SAR) Study

Figure 5:
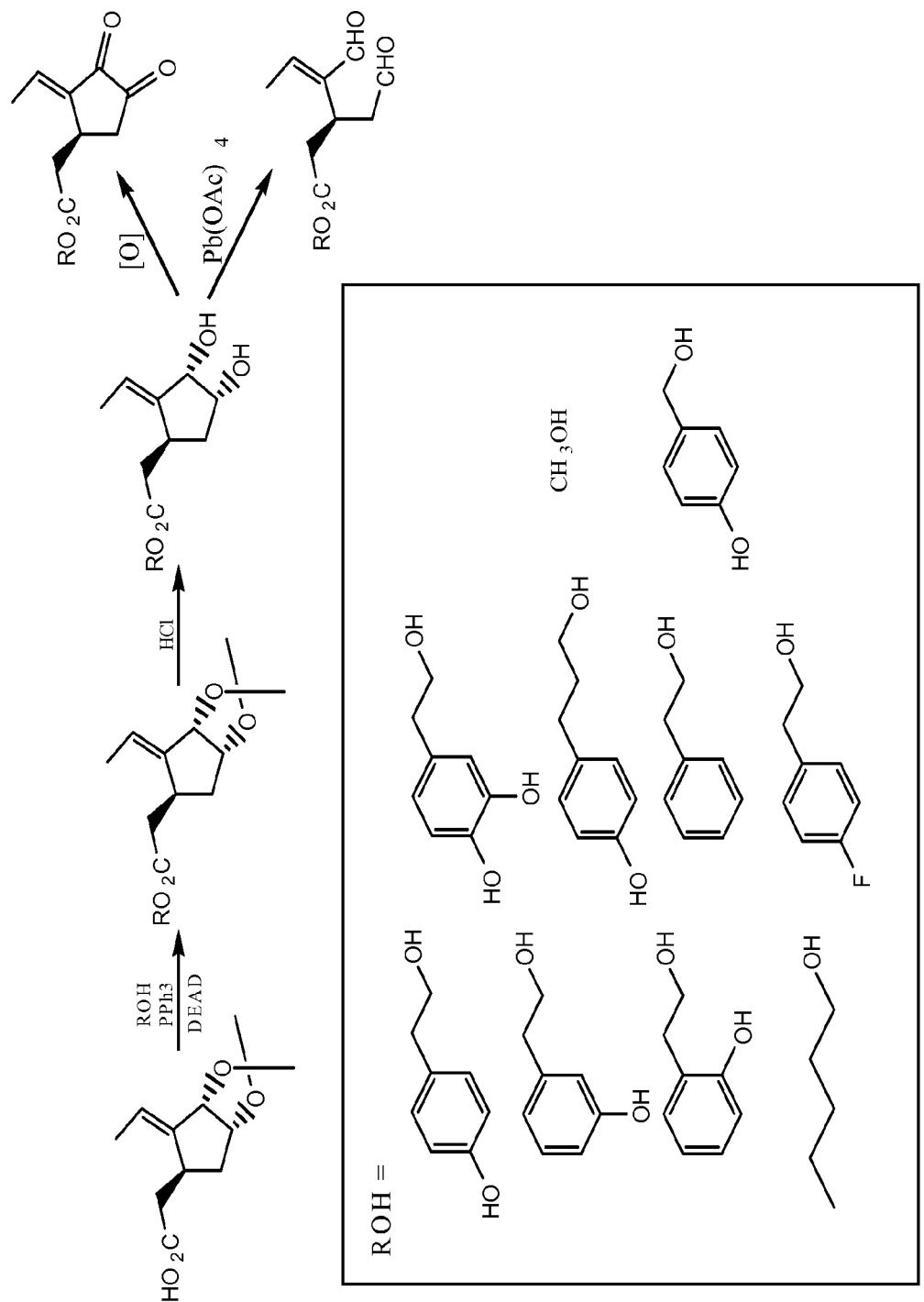
FIG. 5 shows the scheme of a Structure Activity Relationship (SAR) Study.

A Structure Activity Relationship (SAR) Study may be conducted to determine the functional relative activities of oleocanthal derivatives to gain an understanding of the structural basis of oleocanthal irritation. As shown in FIG. 5, a compound having the structure:

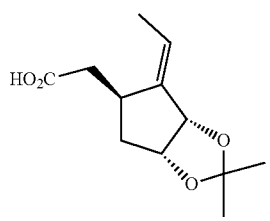 [SMILES: C/C=C1\[C@H](CC(=O)O)C[C@H]2OC(C)(C)O[C@@H]12]

is reacted with a compound selected from the following:

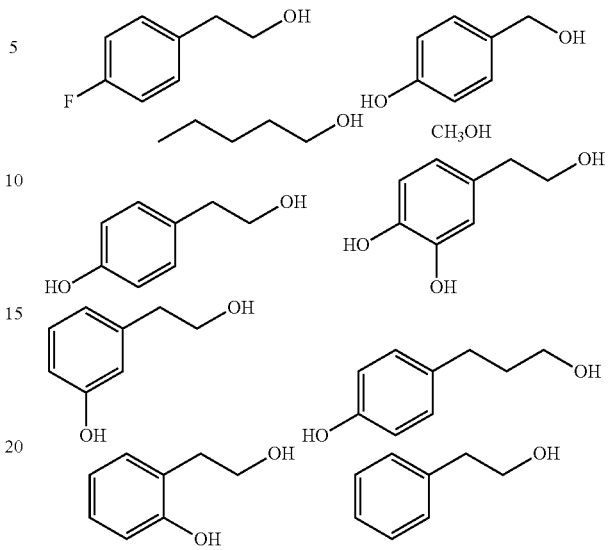

to produce oleocanthal analogs. These compounds are then tested for activity as described herein. The SAR Study allows assignment of relative efficacies and potencies of oleocanthals to each compound and derivation of structural-functional information for rational drug design of oleocanthals.

Activity of synthetic oleocanthal analogs was assessed by measurement of the intracellular calcium level in cultured rat trigeminal neurons. Flavor or taste perception is made up of the sensory experience of three chemical senses: taste, smell, and chemical-induced irritation or pain. This third component is mainly determined by the impact of chemical stimuli that are transmitted to the brain via the trigeminal nerve.

Trigeminal ganglia were harvested from 1-3 day old Sprague-Dawley rat pups. Neurons were dissociated in Hanks Buffered Saline Solution (HBSS) with trypsin (0.0625%) for 15 minutes, collagenase (1 mg/ml) and DNase (0.1 mg/ml) for 45 minutes, and then were separated from myelin/debris using a 15/30/60% Percoll gradient. The neurons were plated on poly-1-lysine/laminin-coated coverslips in modified neurobasal medium supplemented with B27, 100 ng/ml Nerve Growth Factor (NGF) and kept at 37° C., 5% $CO_2$. Following an 18 hour incubation, neurons were loaded with Fura2 AM using 80 mg/ml F-127 Pluronic acid. Intracellular calcium was measured ratiometrically using excitation at 340 and 380 nm and emission at 510 nm. Experiments were performed at 31-32° C. Neurons were stimulated by compounds in Ringers solution (pH=7.34) that flowed over the neurons for 15 sec.

Synthetic (−)oleocanthal and related analogs were dissolved in absolute ethanol and then added to Ringer's solution adjusted at pH=7.34 with a final ethanol concentration of less than 0.1%. The octanol-water partition coefficient (Log P), expressing compound lipophilicity, was calculated based on chemical structure with the Interactive Analysis Log P predictor website. In general, the higher the log P number, the greater the lipophilicity, and the greater the tendency of the compound to partition into the lipid phase of the cell membranes.

Figure 6:
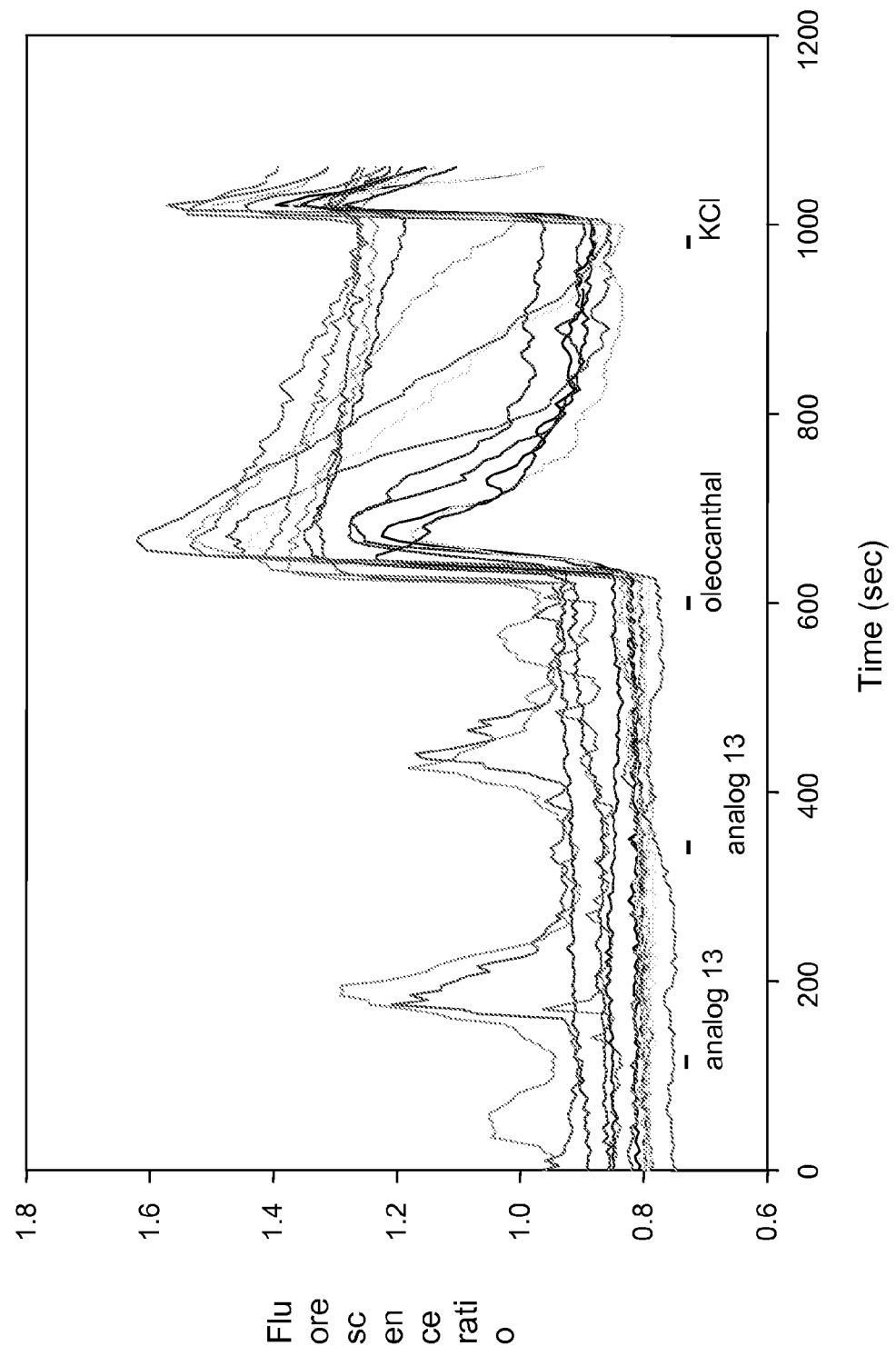
FIG. 6 shows responses of oleocanthal (5 microM) and analog 13 (5 microM) on trigeminal neurons using ratiometric calcium imaging. Each trace represents one cell.
Figure 7:
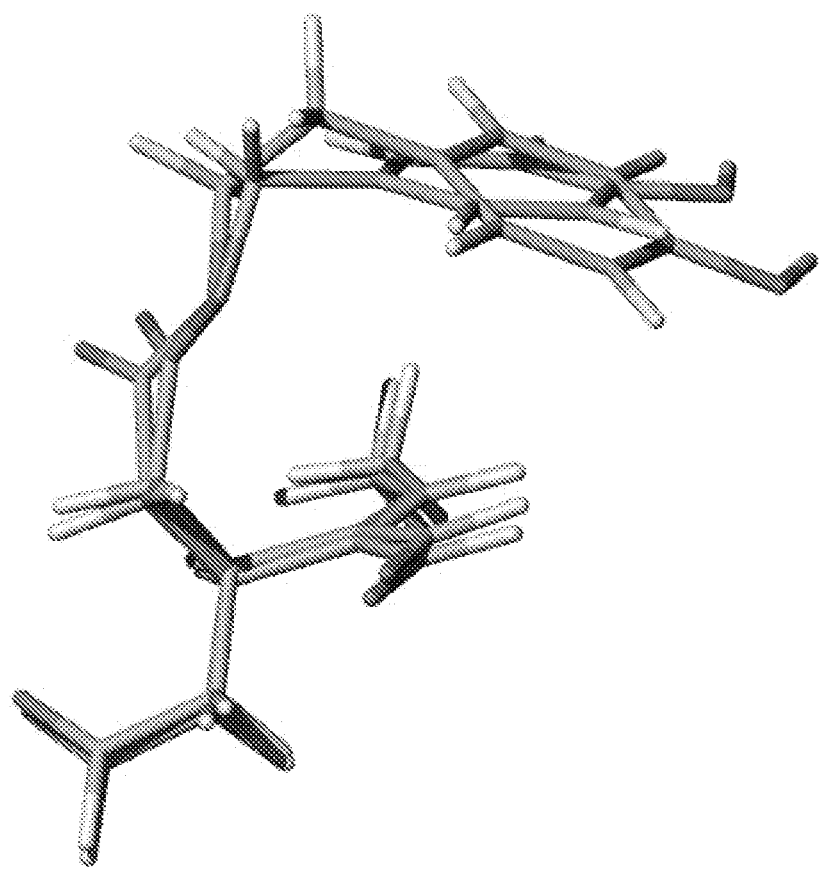
FIG. 7 shows the overlapping 3-dimensional structures of oleocanthal and analog 13.
Figure 8:
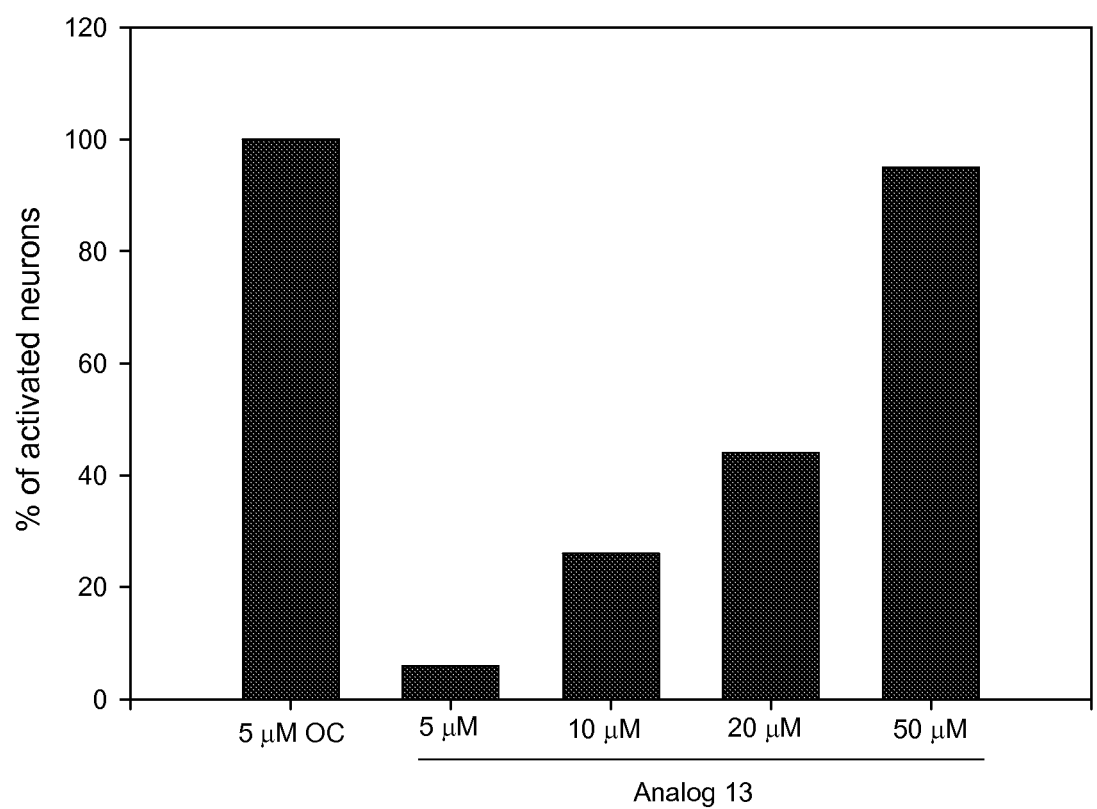
FIG. 8 illustrates the percentage of trigeminal neurons sensitive to 5 micromolar oleocanthal (OC) responding to increasing concentrations of analog 13.
Figure 9:
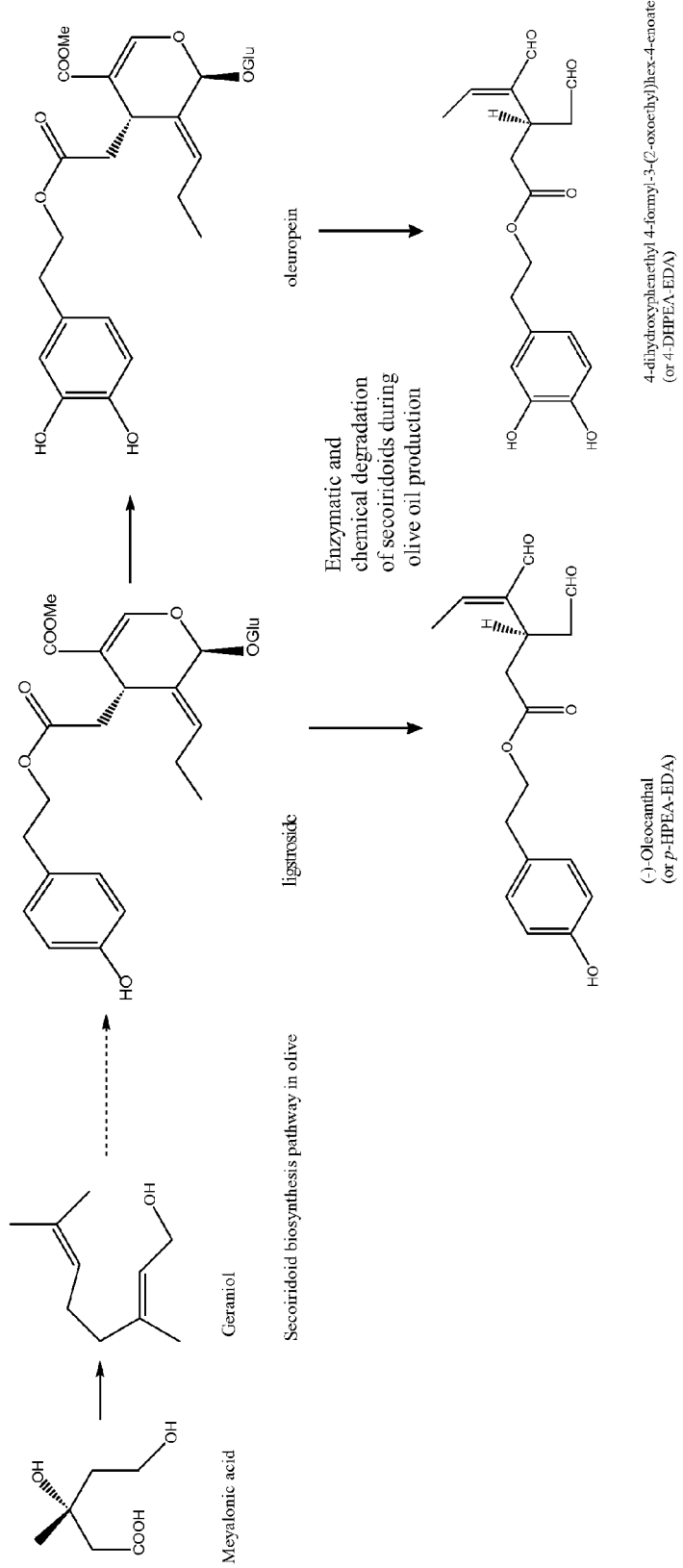
FIG. 9 illustrates oleocanthal and 4-DHPEA-EDA formation during olive oil production by enzymatic and chemical degradation of their respective precursors ligstroside and oleuropein, two glucosylated secoiridoids abundantly synthesized in unripe olives.

Oleocanthal activates rat trigeminal neurons; 5 microM of the olive oil irritant elicits a robust intracellular calcium increase in about 25 to about 35% of cultured rat trigeminal neurons (FIG. 6). Therefore, to assess the irritation potency of oleocanthal analogs and in order to avoid human consumption of unnatural compounds, activity was determined by measurement of the intracellular calcium level in cultured rat trigeminal neurons. Analog structure and activity are summarized in Table 2. Analogs 5, 9, 10 and 12 did not elicit intracellular calcium increase in trigeminal neurons. Thus, both aldehyde groups, as well as unsaturation, are required to maintain full activity. These structural features have been previously shown for a variety of bioactive compounds, notably the often pungent unsaturated dialdehyde sesquiterpenes isolated from plants, mushrooms, termites or algae (Andrewes, P., et al., J. Agric. Food. Chem. 2003; 51:1415-1420). Analog 11 is of particular interest. Like oleocanthal, analog 11 (or 4-DHPEA-EDA) is a secoiridoid derivative naturally present in extra virgin olive oil. Oleocanthal and 4-DHPEA-EDA formation occurs during olive oil production by enzymatic and chemical degradation of their respective precursors ligstroside and oleuropein, two glucosylated secoiridoids abundantly synthesized in unripe olives (FIG. 9). Oleocanthal and 4-DHPEA-EDA are structurally very similar—the sole difference being a second phenolic hydroxyl group in 4-DHPEA-EDA. 4-DHPEA-EDA has been reported to trigger very little oral irritation (Anke, H., et al., Planta Med. 1991; 57:344-346). In the present experiments, both molecules present a similar cellular activity, suggesting an equivalent ability to stimulate the sensory receptor. The lower potency of 4-DHPEA-EDA might be explained by a reduced access to sensory cells due to a lower lipophilicity (Table 2); indeed there is a strong positive relationship between the log P of a solute and the percentage absorption through the mucosa. Analog 13 elicits small responses in trigeminal cells compared to oleocanthal (FIG. 6) although differences in their spatial structure (FIG. 7) and chemical properties appear minimal (Table 2). For the experiment illustrated in FIG. 8, analog 13 (5, 10, 20 and 50 micomolar) was applied on a separate coverslip containing trigeminal neurons and activation was determined. This was followed by application of 5 micromolar oleocanthal to the same four coverslips. For each coverslip, the number of trigeminal neurons responding to oleocanthal was determined and defined as 100%. The number of trigeminal neurons responding to analog 13 corresponded to approximately 6% (5 micromolar analog 13), 25% (10 micromolar analog 13), 45% (20 micromolar analog 13) and 96% (50 micromolar analog 13) of the response to oleocanthal. For each coverslip, 18-20 trigeminal neurons were sensitive to oleocanthal. FIG. 8 shows is that at equi-molar concentrations, analog 13 is much less effective in stimulating trigeminal neurons compared with the reference, oleocanthal: It takes approximately 10 times the concentration of analog 13 to reach the potency of oleocanthal. Analog 13 is very close in structure to oleocanthal (Table 2), lacking only a single carbon. The difference in trigeminal neuron activation by the compounds indicates that the binding site must be quite specific. While not wishing to be bound by any one theory, it is believed that the shorter chain of analog 13 pulls the rigid ring forward creating a steric obstruction to efficacious binding with the receptor.

TABLE 2

Structure, trigeminal neuron activation, and octanol-water partition (Log P) for oleocanthal and related analogs. Assessment of trigeminal neuron activation was based on relatives responses to a single concentration (5 micromolar) of the analogs. The highest scale (+++) was assigned to the analogs that had approximately the same magnitude of response and excited the same number of neurons as oleocanthal. The + responses were weak but detectable and were observed in very few cells. ++ responses were assigned to analogs that elicited intermediate responses to an intermediated number of cells. No detectable response is indicated by 0.

| Structure | TG Neuron Activation | Log P |
|---|---|---|
| 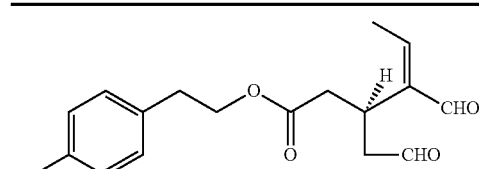<br>(-)-Oleocanthal | +++ | 1.50 |
| 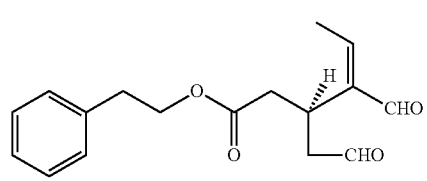<br>Analog 1 | +++ | 1.90 |
| 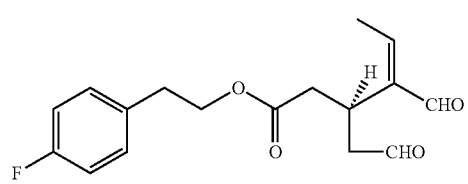 [SMILES: C/C=C(/C=O)[C@@H](CC=O)CC(=O)OCCc1ccc(F)cc1]<br>Analog 2 | +++ | 1.81 |

TABLE 2-continued

Structure, trigeminal neuron activation, and octanol-water partition (Log P) for oleocanthal and related analogs. Assessment of trigeminal neuron activation was based on relatives responses to a single concentration (5 micromolar) of the analogs. The highest scale (+++) was assigned to the analogs that had approximately the same magnitude of response and excited the same number of neurons as oleocanthal. The + responses were weak but detectable and were observed in very few cells. ++ responses were assigned to analogs that elicited intermediate responses to an intermediated number of cells. No detectable response is indicated by 0.

| Structure | TG Neuron Activation | Log P |
|---|---|---|
| Analog 3 | +++ | 2.17 |
| Analog 4 | +++ | 2.03 |
| Analog 5 | 0 | 1.12 |
| Analog 6 | ++ | 0.37 |
| Analog 7 | +++ | 2.17 |
| Analog 8 | +++ | 1.00 |

TABLE 2-continued

Structure, trigeminal neuron activation, and octanol-water partition (Log P) for oleocanthal and related analogs. Assessment of trigeminal neuron activation was based on relatives responses to a single concentration (5 micromolar) of the analogs. The highest scale (+++) was assigned to the analogs that had approximately the same magnitude of response and excited the same number of neurons as oleocanthal. The + responses were weak but detectable and were observed in very few cells. ++ responses were assigned to analogs that elicited intermediate responses to an intermediated number of cells. No detectable response is indicated by 0.

| Structure | TG Neuron Activation | Log P |
|---|---|---|
| Analog 9 | + | 1.33 |
| Analog 10 | 0 | 0.95 |
| Analog 11 (4-DHPEA-EDA) | +++ | −0.30 |
| Analog 12 | 0 | 1.24 |
| Analog 13 | + | 1.69 |

What is claimed:

1. An anti-inflammatory composition comprising a therapeutically effective amount of a compound that is

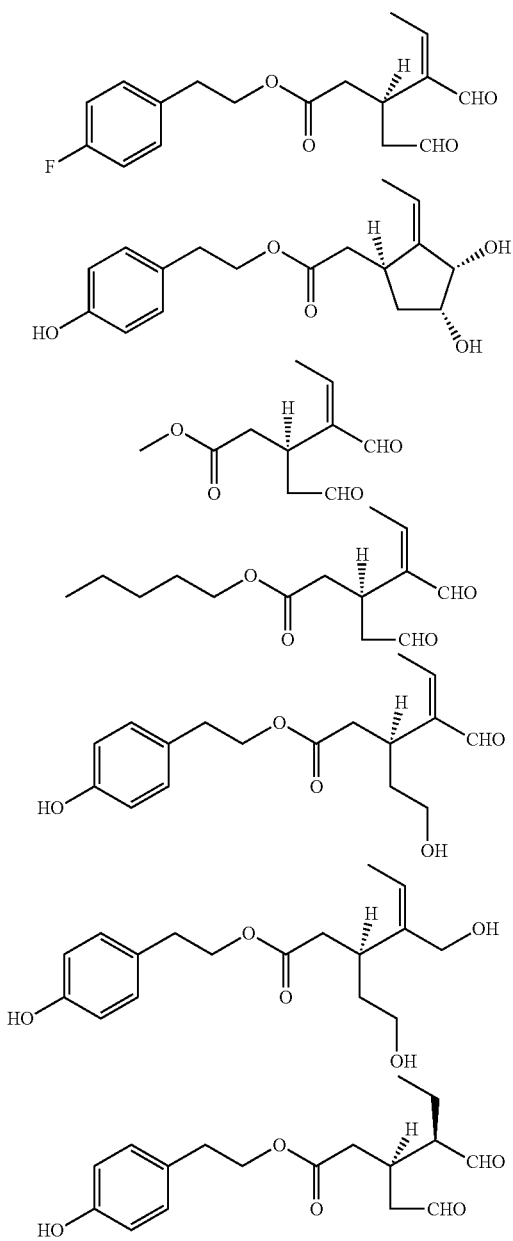

and a pharmaceutically acceptable carrier.

2. A method of treating a patient with an inflammatory disorder comprising administering to the patient an effective amount of a composition comprising a compound that is:

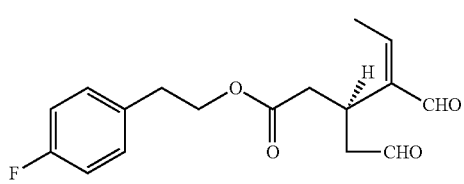

-continued

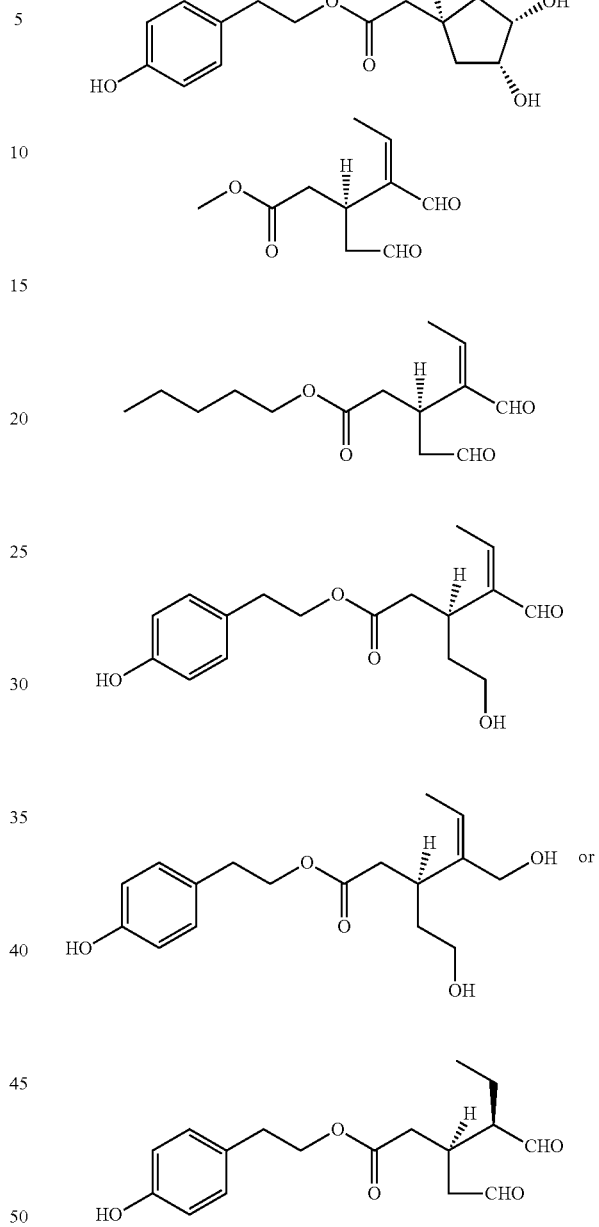

and wherein said composition alleviates inflammation in said patient.

3. The method of claim 2 wherein said inflammatory disorder is selected from the group consisting of psoriasis, cancer, asthma, allergic rhinitis, respiratory distress syndrome, inflammatory bowel disease, Chron's disease, gastritis, irritable bowel syndrome, ulcerative colitis, migraine, periarteritis nodosa, thyroiditis, aplastic anemia, Hodgkin's disease, sclerodoma, type I diabetes, myasthenia gravis, multiple sclerosis, sorcoidosis, ischemic kidney disease, nephrotic syndrome, Bechet's syndrome, polymyositis, gingivitis, conjunctivitis, vascular disease myocardial ischemia, heart disease, and stroke.

4. The method of claim 2, wherein the compound is
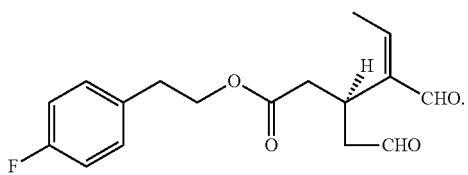
5. The method of claim 2, wherein the compound is
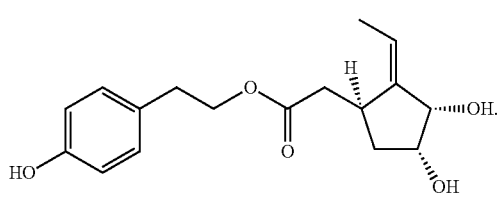 [SMILES: C/C=C1\[C@H](CC(=O)OCCc2ccc(O)cc2)C[C@@H](O)[C@H]1O]
6. The method of claim 2, wherein the compound is
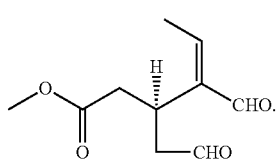
7. The method of claim 2, wherein the compound is
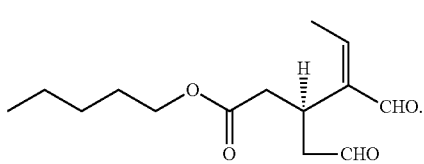 [SMILES: C/C=C(/C=O)[C@@H](CC=O)CC(=O)OCCCCC]
8. The method of claim 2, wherein the compound is
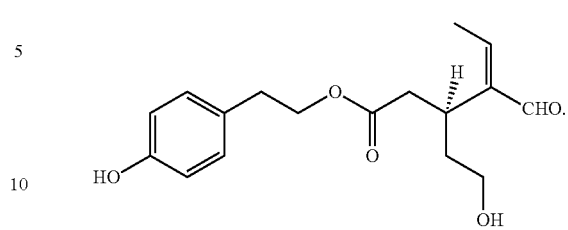
9. The method of claim 2, wherein the compound is
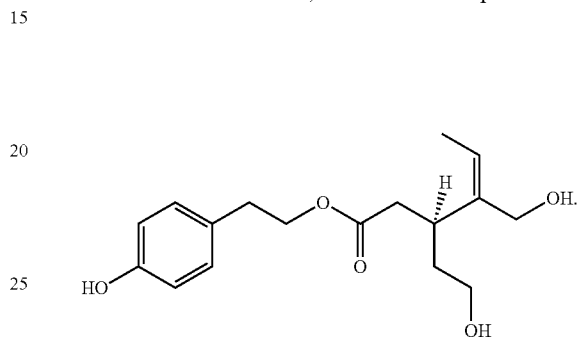
10. The method of claim 2, wherein the compound is
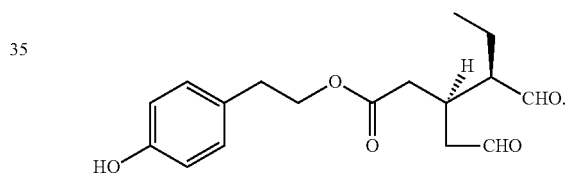
* * * * *

UNITED STATES PATENT AND TRADEMARK OFFICE
CERTIFICATE OF CORRECTION

PATENT NO. : 8,586,632 B2
APPLICATION NO. : 12/597053
DATED : November 19, 2013
INVENTOR(S) : Peyrot Des Gachons et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1021 days.

Signed and Sealed this
Twenty-second Day of September, 2015

Michelle K. Lee
*Director of the United States Patent and Trademark Office*